(12) United States Patent
Maharbiz et al.

(10) Patent No.: US 11,033,746 B2
(45) Date of Patent: Jun. 15, 2021

(54) IMPLANTS USING ULTRASONIC COMMUNICATION FOR NEURAL SENSING AND STIMULATION

(71) Applicant: IOTA BIOSCIENCES, INC., Berkeley, CA (US)

(72) Inventors: Michel M. Maharbiz, El Cerrito, CA (US); Ryan Neely, Berkeley, CA (US); Joshua Kay, Berkeley, CA (US); Jose M. Carmena, Berkeley, CA (US)

(73) Assignee: IOTA BIOSCIENCES, INC., Berkeley, CA (US)

( * ) Notice: Subject to any disclaimer, the term of this patent is extended or adjusted under 35 U.S.C. 154(b) by 209 days.

(21) Appl. No.: 16/389,876

(22) Filed: Apr. 19, 2019

(65) Prior Publication Data

US 2019/0321644 A1   Oct. 24, 2019

Related U.S. Application Data

(60) Provisional application No. 62/660,112, filed on Apr. 19, 2018.

(51) Int. Cl.
*A61N 1/372* (2006.01)
*A61N 1/36* (2006.01)
(Continued)

(52) U.S. Cl.
CPC ....... *A61N 1/37217* (2013.01); *A61N 1/3605* (2013.01); *A61N 1/3787* (2013.01);
(Continued)

(58) Field of Classification Search
None
See application file for complete search history.

(56) References Cited

U.S. PATENT DOCUMENTS

| 5,282,468 A | 2/1994 | Klepinski |
| 6,170,488 B1 | 1/2001 | Spillman, Jr. |

(Continued)

FOREIGN PATENT DOCUMENTS

| EP | 2515996 | 10/2012 |
| EP | 2667942 | 12/2013 |

(Continued)

OTHER PUBLICATIONS

J. -. Tsai, K. -. Huang, J. -. Wang, S. -. Liu and P. Li, "Ultrasonic wireless power and data communication for neural stimulation," 2011 IEEE International Ultrasonics Symposium, Orlando, FL, USA, 2011, pp. 1052-1055, doi: 10.1109/ULTSYM.2011.0258. (Year: 2011).*

(Continued)

*Primary Examiner* — Paula J Stice
(74) *Attorney, Agent, or Firm* — Morrison & Foerster LLP

(57) ABSTRACT

Described herein is an implantable medical device that includes a body having one or more ultrasonic transducers configured to receive ultrasonic waves and convert energy from the ultrasonic waves into an electrical energy, two or more electrodes in electrical communication with the ultrasonic transducer, and a clip attached to the body that is configured to at least partially surround a nerve and/or a filamentous tissue and position the two or more electrodes in electrical communication with the nerve. In certain examples, the implantable medical device includes two ultrasonic transducers with orthogonal polarization axes. Also described herein are methods for treating incontinence in a subject by converting energy from ultrasonic waves into an electrical energy that powers a full implanted medical device, and electrically stimulating a tibial nerve, a pudendal (Continued)

nerve, or a sacral nerve, or a branch thereof, using the fully implanted medical device.

17 Claims, 8 Drawing Sheets

(51) Int. Cl.
    *A61N 1/378*     (2006.01)
    *A61N 1/04*     (2006.01)
    *A61B 5/00*     (2006.01)

(52) U.S. Cl.
    CPC ..... *A61N 1/37276* (2013.01); *A61N 1/37282* (2013.01); *A61B 5/4836* (2013.01); *A61N 1/0456* (2013.01)

(56) References Cited

U.S. PATENT DOCUMENTS

| | | |
|---|---|---|
| 6,200,265 B1 | 3/2001 | Walsh |
| 6,885,888 B2 | 4/2005 | Rezai |
| 7,024,248 B2 | 4/2006 | Penner |
| 7,283,874 B2 | 10/2007 | Penner |
| 7,616,990 B2 | 11/2009 | Chavan |
| 7,617,001 B2 | 11/2009 | Penner |
| 7,634,318 B2 | 12/2009 | Tran |
| 7,756,587 B2 | 7/2010 | Penner |
| 7,757,565 B2 | 7/2010 | Chakrabartty |
| 7,778,704 B2 | 8/2010 | Rezai |
| 7,794,499 B2 | 9/2010 | Navarro |
| 7,894,907 B2 | 2/2011 | Echt |
| 7,899,542 B2 | 3/2011 | Cowan |
| 8,340,778 B2 | 12/2012 | Tran |
| 8,412,338 B2 | 4/2013 | Faltys |
| 8,478,428 B2 | 7/2013 | Cowley |
| 8,494,642 B2 | 7/2013 | Cowan |
| 8,494,643 B2 | 7/2013 | Cowan |
| 8,577,460 B2 | 11/2013 | Penner |
| 8,612,002 B2 | 12/2013 | Faltys |
| 8,660,648 B2 | 2/2014 | Chavan |
| 8,774,928 B2 | 7/2014 | Towe |
| 8,788,034 B2 | 7/2014 | Levine |
| 8,849,412 B2 | 9/2014 | Perryman |
| 8,855,767 B2 | 10/2014 | Faltys |
| 8,874,233 B2 | 10/2014 | Mclaughlin |
| 8,886,339 B2 | 11/2014 | Faltys |
| 8,903,501 B2 | 12/2014 | Perryman |
| 8,934,972 B2 | 1/2015 | Penner |
| 8,996,116 B2 | 3/2015 | Faltys |
| 9,162,064 B2 | 10/2015 | Faltys |
| 9,174,041 B2 | 11/2015 | Faltys |
| 9,174,044 B2 | 11/2015 | Mclaughlin |
| 9,199,089 B2 | 12/2015 | Perryman |
| 9,211,409 B2 | 12/2015 | Tracey |
| 9,211,410 B2 | 12/2015 | Levine |
| 9,220,897 B2 | 12/2015 | Perryman |
| 9,242,103 B2 | 1/2016 | Perryman |
| 9,409,030 B2 | 8/2016 | Perryman |
| 9,544,068 B2 | 1/2017 | Arbabian |
| 9,566,449 B2 | 2/2017 | Perryman |
| 9,597,508 B2 | 3/2017 | Mclaughlin |
| 9,610,442 B2 | 4/2017 | Yoo |
| 9,623,253 B2 | 4/2017 | Perryman |
| 9,700,716 B2 | 7/2017 | Faltys |
| 9,717,921 B2 | 8/2017 | Perryman |
| 9,731,141 B2 | 8/2017 | Tran |
| 9,757,571 B2 | 9/2017 | Perryman |
| 9,789,314 B2 | 10/2017 | Perryman |
| 9,802,055 B2 | 10/2017 | Reinke |
| 9,833,621 B2 | 12/2017 | Levine |
| 9,849,286 B2 | 12/2017 | Levine |
| 9,925,384 B2 | 3/2018 | Perryman |
| 9,974,593 B2 | 5/2018 | Barman |
| 9,974,965 B2 | 5/2018 | Perryman |
| 9,993,651 B2 | 6/2018 | Faltys |
| 10,014,570 B2 | 7/2018 | Arbabian |
| 10,118,054 B2 | 11/2018 | Maharbiz |
| 10,177,606 B2 | 1/2019 | Charthad |
| 10,201,706 B2 | 2/2019 | Schwab |
| 10,220,203 B2 | 3/2019 | Faltys |
| 10,286,206 B2 | 5/2019 | Johnson et al. |
| 10,300,309 B2 | 5/2019 | Maharbiz |
| 10,300,310 B2 | 5/2019 | Maharbiz |
| 10,576,305 B2 | 3/2020 | Maharbiz |
| 10,682,530 B2 | 6/2020 | Maharbiz |
| 10,744,347 B2 | 8/2020 | Maharbiz |
| 10,765,865 B2 | 9/2020 | Maharbiz |
| 10,898,736 B2 | 1/2021 | Maharbiz et al. |
| 2005/0075701 A1 | 4/2005 | Shafer |
| 2005/0075702 A1 | 4/2005 | Shafer |
| 2006/0136004 A1 | 6/2006 | Cowan |
| 2006/0287678 A1 | 12/2006 | Shafer |
| 2007/0093875 A1 | 4/2007 | Chavan |
| 2008/0108915 A1 | 5/2008 | Penner |
| 2009/0018403 A1 | 1/2009 | Black |
| 2009/0210042 A1 | 8/2009 | Kowalczewski |
| 2009/0248097 A1 | 10/2009 | Tracey |
| 2009/0275997 A1 | 11/2009 | Faltys |
| 2010/0268078 A1 | 10/2010 | Scarantino |
| 2011/0054569 A1 | 3/2011 | Zitnik |
| 2013/0062527 A1 | 3/2013 | Hyde |
| 2013/0238044 A1 | 9/2013 | Penner |
| 2013/0310909 A1 | 11/2013 | Simon |
| 2013/0324891 A1 | 12/2013 | Towe |
| 2014/0094887 A1 | 4/2014 | True |
| 2014/0253435 A1 | 9/2014 | Boser |
| 2014/0336474 A1 | 11/2014 | Arbabian |
| 2014/0336727 A1 | 11/2014 | Perryman |
| 2015/0073510 A1 | 3/2015 | Perryman |
| 2015/0112233 A1 | 4/2015 | Towe |
| 2015/0241447 A1 | 8/2015 | Zitnik |
| 2015/0297900 A1 | 10/2015 | Perryman |
| 2016/0007893 A1 | 1/2016 | Roberts |
| 2016/0023003 A1 | 1/2016 | Perryman |
| 2016/0038741 A1 | 2/2016 | Perryman |
| 2016/0038769 A1 | 2/2016 | Sullivan |
| 2016/0045743 A1 | 2/2016 | Liu |
| 2016/0067497 A1 | 3/2016 | Levine |
| 2016/0114165 A1 | 4/2016 | Levine |
| 2016/0235329 A1 | 8/2016 | Bernstein |
| 2016/0331952 A1 | 11/2016 | Faltys |
| 2016/0331962 A1 | 11/2016 | Schwab |
| 2017/0001003 A1 | 1/2017 | Pivonka |
| 2017/0007853 A1 | 1/2017 | Alford |
| 2017/0095198 A1 | 4/2017 | Towe |
| 2017/0095667 A1 | 4/2017 | Yakovlev |
| 2017/0100588 A1 | 4/2017 | Schwab |
| 2017/0100589 A1 | 4/2017 | Schwab |
| 2017/0100604 A1 | 4/2017 | Schwab |
| 2017/0100605 A1 | 4/2017 | Schwab |
| 2017/0117753 A1 | 4/2017 | Charthad |
| 2017/0125892 A1 | 5/2017 | Arbabian |
| 2017/0173328 A1 | 6/2017 | Ostroff |
| 2017/0197082 A1 | 7/2017 | Pang |
| 2017/0202467 A1 | 7/2017 | Zitnik et al. |
| 2018/0008828 A1 | 1/2018 | Perryman |
| 2018/0021214 A1 | 1/2018 | Tracey |
| 2018/0021580 A1 | 1/2018 | Tracey |
| 2018/0027077 A1 | 1/2018 | Melodia |
| 2018/0055393 A1 | 3/2018 | Cantwell |
| 2018/0085605 A1 | 3/2018 | Maharbiz |
| 2018/0117319 A1 | 5/2018 | Chew |
| 2018/0117320 A1 | 5/2018 | Levine |
| 2018/0169423 A1 | 6/2018 | Perryman |
| 2018/0236248 A1 | 8/2018 | Perryman |
| 2018/0264277 A1 | 9/2018 | Perryman |
| 2018/0289970 A1 | 10/2018 | Faltys |
| 2019/0022427 A1 | 1/2019 | Maharbiz |
| 2019/0022428 A1 | 1/2019 | Maharbiz |
| 2019/0150881 A1 | 5/2019 | Maharbiz |
| 2019/0150882 A1 | 5/2019 | Maharbiz |
| 2019/0150883 A1 | 5/2019 | Maharbiz |
| 2019/0150884 A1 | 5/2019 | Maharbiz |
| 2019/0321640 A1 | 10/2019 | Carmena |

(56) References Cited

U.S. PATENT DOCUMENTS

| | | |
|---|---|---|
| 2020/0023208 A1 | 1/2020 | Maharbiz |
| 2020/0023209 A1 | 1/2020 | Maharbiz |
| 2020/0114175 A1 | 4/2020 | Maharbiz |
| 2020/0230441 A1 | 7/2020 | Maharbiz |
| 2020/0289857 A1 | 9/2020 | Maharbiz |
| 2020/0324148 A1 | 10/2020 | Maharbiz |

FOREIGN PATENT DOCUMENTS

| | | |
|---|---|---|
| EP | 2694154 | 2/2014 |
| EP | 2741810 | 6/2014 |
| EP | 2162185 B1 | 7/2015 |
| EP | 1648559 B1 | 9/2015 |
| EP | 2928557 | 10/2015 |
| EP | 2707094 B1 | 2/2016 |
| EP | 2337609 B1 | 8/2016 |
| EP | 2755718 B1 | 12/2017 |
| EP | 3259015 | 12/2017 |
| EP | 3259017 | 12/2017 |
| EP | 2736592 B1 | 1/2018 |
| EP | 3285856 | 2/2018 |
| EP | 2651431 B1 | 3/2018 |
| EP | 3294376 | 3/2018 |
| EP | 3338855 A1 | 6/2018 |
| EP | 2440284 B1 | 9/2018 |
| EP | 3403690 A1 | 11/2018 |
| WO | 2005032653 A1 | 4/2005 |
| WO | 2007050657 A1 | 5/2007 |
| WO | 2007090159 A1 | 8/2007 |
| WO | 2009146030 A1 | 12/2009 |
| WO | 2010059617 A2 | 5/2010 |
| WO | 2010059617 A3 | 5/2010 |
| WO | 2010144578 A2 | 12/2010 |
| WO | 2010144578 A3 | 12/2010 |
| WO | 2011028763 A2 | 3/2011 |
| WO | 2011028763 A3 | 3/2011 |
| WO | 2011079309 A2 | 6/2011 |
| WO | 2011079309 A3 | 6/2011 |
| WO | 2012057868 A1 | 5/2012 |
| WO | 2012083259 A2 | 6/2012 |
| WO | 2012083259 A3 | 6/2012 |
| WO | 2012103519 A2 | 8/2012 |
| WO | 2012103519 A3 | 8/2012 |
| WO | 2012138782 A1 | 10/2012 |
| WO | 2012154865 A2 | 11/2012 |
| WO | 2012154865 A3 | 11/2012 |
| WO | 2013019757 A2 | 2/2013 |
| WO | 2013019757 A3 | 2/2013 |
| WO | 2013025632 A1 | 2/2013 |
| WO | 2013040549 A1 | 3/2013 |
| WO | 2013044207 A1 | 3/2013 |
| WO | 2013134479 A1 | 9/2013 |
| WO | 2014089299 A2 | 6/2014 |
| WO | 2014089299 A3 | 6/2014 |
| WO | 2014153218 A1 | 9/2014 |
| WO | 2014153219 A1 | 9/2014 |
| WO | 2014153223 A1 | 9/2014 |
| WO | 2014153228 A1 | 9/2014 |
| WO | 2014169145 A1 | 10/2014 |
| WO | 2015127476 A1 | 8/2015 |
| WO | 2015142842 A2 | 9/2015 |
| WO | 2015142842 A3 | 9/2015 |
| WO | 2016028608 A1 | 2/2016 |
| WO | 2016134197 A1 | 8/2016 |
| WO | 2016134199 A1 | 8/2016 |
| WO | 2016170510 A1 | 10/2016 |
| WO | 2016183353 A1 | 11/2016 |
| WO | 2016187114 A1 | 11/2016 |
| WO | 2018009905 A2 | 1/2018 |
| WO | 2018009905 A3 | 1/2018 |
| WO | 2018009908 A1 | 1/2018 |
| WO | 2018009910 A1 | 1/2018 |
| WO | 2018009911 A1 | 1/2018 |
| WO | 2018009912 A1 | 1/2018 |
| WO | 2018017591 A1 | 1/2018 |
| WO | 2018081763 A1 | 5/2018 |
| WO | 2018081826 A1 | 5/2018 |
| WO | 2018087193 A1 | 5/2018 |
| WO | 2018089895 A2 | 5/2018 |
| WO | 2018089895 A3 | 5/2018 |
| WO | 2018118857 A1 | 6/2018 |
| WO | 2018118860 A1 | 6/2018 |
| WO | 2018118861 A1 | 6/2018 |
| WO | 2018118864 A1 | 6/2018 |
| WO | 2018118866 A1 | 6/2018 |
| WO | 2019075203 A1 | 4/2019 |
| WO | 2019204769 A1 | 10/2019 |
| WO | 2020047152 A1 | 3/2020 |
| WO | 2020117967 A1 | 6/2020 |
| WO | 2020142732 A1 | 7/2020 |
| WO | 2020142733 A1 | 7/2020 |

OTHER PUBLICATIONS

Bertrand, A. et al. (Aug. 2014). "Beamforming Approaches for Untethered, Ultrasonic Neural Dust Motes for Cortical Recording: A Simulation Study," IEEE EMBC, pp. 2625-2628.

Beyer, G.P. et al. (Jan. 1, 2008). "An Implantable MOSFET Dosimeter for the Measurement of Radiation Dose in Tissue During Cancer Therapy," IEEE Sensors Journal 8(1):38-51.

Celinskis, D.et al. (Aug. 26, 2014). "Wireless Impedance Measurements for Monitoring Peripheral Vascular Disease," 36th Annual International Conference of the IEEE Engineering in Medicine and Biology Society pp.

Grossman, N. et al. (Jun. 1, 2017). "Noninvasive Deep Brain Stimulation via Temporally Interfering Electric Fields," Cell 169:1029-1041.

International Preliminary Report on Patentability, dated Oct. 29, 2020 for PCT Application No. PCT/US2019/028385, filed Apr. 19, 2019, 7 pages.

International Search Report and Written Opinion, dated Aug. 29, 2019 for PCT Application No. PCT/US2019/028385, filed Apr. 19, 2019, 23 pages.

Kay, J. (May 4, 2017). "Rodent Wearable Ultrasound Interrogation System for Wireless Neural Recording", Berkeley EECS, Technical Report No. UCS/EECS-2017-27, 50 pages.

Mazzilli, F. et al. (Aug. 31-Sep. 4, 2010). "In-Vitro Platform to Study Ultrasound as Source for Wireless Energy Transfer and Communication for Implanted Medical Devices," 32nd Annual International Conference of the IEEE EMBS, pp. 3751-3754.

Peisino, M. (May 17, 2013). "Deeply Implanted Medical Device Based on a Novel Ultrasonic Telemetry Technology," École Polytechnique Fédérale De Lausanne pp. 148.

Piech, D.K. et al. (2017). "Rodent Wearable Ultrasound System for Wireless Neural Recording," 39th Annual International Conference of the IEEE Engineering in Medicine and Biology Society, EMBC, 5 pages.

Seo, D. (May 1, 2016). "Design of Ultrasonic Power Link for Neural Dust", Technical Report No. UCB/EECS-2016-21, Electrical Engineering and Computer Sciences University of California at Berkeley, 71 pages.

Seo, D. et al. (2015). "Ultrasonic Beamforming System for Interrogating Multiple Implantable Sensors," IEEE, pp. 2673-2676.

Seo, D. et al. (Apr. 1, 2015, e-pub. Aug. 7, 2014). "Model Validation of Untethered, Ultrasonic Neural Dust Motes for Cortical Recording," J. of Neuroscience Methods 244:114-122.

Seo, D. et al. (Aug. 3, 2016). "Wireless Recording in the Peripheral Nervous System with Ultrasonic Neural Dust," Neuron 91:529-539.

Seo, D. et al. (Jul. 8, 2013). "Neural Dust: Ultrasonic Low Power Solution for Chronic Brain-Machine Interfaces," Dept. of Electrical Engineering and Computer Sciences Berkley, CA. pp. 1-11.

Tang, H.-Y. et al. (Dec. 2015). "Miniaturizing Ultrasonic System for Portable Health Care and Fitness," IEEE Transactions on Biomedical Circuits and Systems 9(6):767-776.

Taylor, J. et al. (2004). "Multiple-Electrode Nerve Cuffs for Low-Velocity and Velocity-Selective Neural Recording," Medical & Biological Engineering & Computing 42:634-643.

U.S. Appl. No. 16/754,543, Arbabian et al., filed Apr. 8, 2020.

(56) References Cited

OTHER PUBLICATIONS

U.S. Appl. No. 17/272,217, Carmena et al., filed Aug. 26, 2021.
Weissleder, R. et al. (May 1, 2001). "Molecular Imaging," Radiology, Radiological Society of North America, Inc. 219(2):316-333.
Wodlinger, B. et al. (Oct. 2009). "Localization and Recovery of Perifpheral Neural Sources With Beamforming Algorithms," IEEE Transactions on Neural Systems and Rehabilitation Engineering 17(5):461-468, 18 pages.

\* cited by examiner

IMPLANTS USING ULTRASONIC COMMUNICATION FOR NEURAL SENSING AND STIMULATION

CROSS-REFERENCE TO RELATED APPLICATION

This application claims priority benefit to U.S. Provisional Application No. 62/660,112, filed on Apr. 19, 2018, which is incorporated herein by reference for all purposes.

TECHNICAL FIELD

The present invention relates to implantable medical devices that are powered by ultrasonic waves, and methods of using the implantable medical device.

BACKGROUND

The peripheral nervous system of an individual operates activity of vital organs and physiological homeostasis with tight control. Electrical pulses transmitted through nerves can alter, for example, pulse rates, inflammation, and bladder or bowel control. Certain medical conditions can arise when these neural signals fail to properly control the body, either by over-stimulating or under-stimulating target organs.

Invasive methods have been developed for treating abnormal physiological activity by controlling the electrical signals of the peripheral nervous system. Such methods can include implanting electrodes into the body of a patient, with the tips of the electrodes contacting target nerves. These electrodes generally have long leads that attach to an external device, which subject the patient to substantial risk of infection or displacement of the electrodes. Additionally, because many of the methods are so invasive, certain treatments are limited to clinical settings, and cannot be used as an at-home remedy. Wholly implantable devices have been developed for less invasive treatment, but such devices are too large to be placed in many locations of the body. Therefore, the implanted devices require the use of long leads, which can be displaced or break. Such implanted devices are also implanted to stimulate upstream nerves, such as the vagus nerve, which leads to significant side effects due off target electrical stimulation.

There continues to be a need for implantable devices that can stimulate specific nerves in a controlled manner and with limited risks and side effects.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE INVENTION

Described herein is an implantable medical device, comprising (a) a body comprising an ultrasonic transducer configured to receive ultrasonic waves and convert energy from the ultrasonic waves into an electrical energy that powers the device; (b) two or more electrodes in electrical communication with the ultrasonic transducer; and (c) a clip attached to the body that is configured to at least partially surround a nerve and position the two or more electrodes in electrical communication with the nerve. In some embodiments, the clip is configured to at least partially surround the nerve and a filamentous tissue attached to the nerve. In some embodiments, the filamentous tissue is a blood vessel.

In some embodiments of the implantable medical device, the clip comprises a plurality of flexible legs that extend below the body. In some embodiments, the implantable device comprises a hook or loop configured to maneuver at least one of the flexible legs in response to maneuvering the hook or loop. In some embodiments, the hook or loop is positioned at a terminus of one of the flexible legs. In some embodiments, the hook or loop is positioned proximal to the body.

In some embodiments of the implantable medical device, the flexible legs are curved. In some embodiments, the legs extend away from the body before curving toward the body as the legs extend below the body.

In some embodiments of the implantable medical device, the plurality of flexible legs comprises at least one pair of legs, wherein the pair of legs comprises a first leg and a second leg that extend away from and below the body in opposite directions. In some embodiments, the first leg and the second leg are connected by a crossbar connected to the body. In some embodiments, the crossbar is connected to the body of the device through a flexible member. In some embodiments, the flexible member is a hinge. In some embodiments, the device comprises two pairs of legs, wherein each pair of leg is positioned on opposite sides of the body. In some embodiments, the legs are attached to the body through a bottom surface of the body. In some embodiments, the legs are attached to the body through a sidewall of the body.

In some embodiments of the implantable medical device, the legs comprise a metal, metal alloy, ceramic, silicon, or a non-polymeric material. In some embodiments, the legs comprise an elastomeric coating or a non-elastomeric polymer coating. In some embodiments, the coating is bioinert. In some embodiments, the coating is a silicone, a poly(p-xylylene) polymer, or a polyimide. In some embodiments, at least one of the legs comprises an outer surface coated with the elastomeric coating or the non-elastomeric polymer coating and an inner surface comprising at least one electrode that is not coated with the elastomeric coating or the non-elastomeric polymer coating.

In some embodiments of the implantable medical device, the body comprises a bottom surface, and the two or more electrodes are terminate on the bottom of the body. In some embodiments, the two or more electrodes are positioned on the clip. In some embodiments, the clip comprises a plurality of flexible legs that extend below the body, and the two or more electrodes are positioned on the flexible legs.

In some embodiments of the implantable medical device, the body comprises a housing. In some embodiments, the housing comprises or is coated with a bioinert material. In some embodiments, the housing comprises the bioinert material, and wherein the bioinert material of the housing comprises titanium or a ceramic.

In some embodiments of the implantable medical device, the body comprises an integrated circuit electrically connected to the ultrasonic transducer and the two or more electrodes. In some embodiments, the integrated circuit comprises an energy storage circuit comprising a capacitor.

In some embodiments of the implantable medical device, the body is about 5 mm or less in length in the longest dimension.

In some embodiments of the implantable medical device, the ultrasonic transducer is configured to emit an ultrasonic backscatter that encodes data. In some embodiments, the data comprises information related to a detected neural activity, a measured physiological condition, a device status, or an emitted electrical pulse.

In some embodiments of the implantable medical device, the implantable medical device is configured to emit an electrical pulse to the nerve.

In some embodiments of the implantable medical device, the ultrasonic transducer is configured to receive ultrasonic waves that encode instructions for operating the implantable device. In some embodiments, the instructions comprise a trigger signal that operates the implantable device to emit an electrical pulse to the nerve.

Also described herein is a method of implanting a medical device in a subject, the device comprising a body comprising an ultrasonic transducer configured to receive ultrasonic waves and convert energy from the ultrasonic waves into an electrical energy that powers the device, electrodes in electrical communication with the ultrasonic transducer, and a clip attached to the body, wherein the clip comprises a plurality of flexible legs, the method comprising (a) outwardly flexing one or more legs of the clip; (b) positioning the electrodes to be in electrical communication with a nerve; and (c) releasing the one or more legs of the clip, where the one or more legs at least partially surrounds the nerve and maintains the electrodes in electrical communication with the nerve upon release. In some embodiments, the plurality of legs at least partially surrounds the nerve and a filamentous tissue attached to the nerve. In some embodiments, the filamentous tissue is a blood vessel. In some embodiments, the device is laparoscopically implanted in the subject. In some embodiments, the clip exerts an inward pressure on the nerve. In some embodiments, the clip allows for rotational movement around the nerve. In some embodiments, the legs exert a pressure on the nerve or the filamentous tissue of about 1 MPa or less.

In some embodiments of a method of implanting a medical device in a subject, the nerve is an autonomic nerve. In some embodiments, the nerve is a sympathetic nerve. In some embodiments, nerve is a mesenteric nerve, a splenic nerve, a sciatic nerve, a tibial nerve, a celiac ganglion, or a sacral nerve.

In some embodiments of a method of implanting the medical device in a subject, the plurality of legs extend below the body. In some embodiments, outwardly flexing one or more legs of the clip comprises maneuvering one or more hooks or loops connected to the one or more legs. In some embodiments, the legs are curved. In some embodiments, the legs extend away from the body before curving toward the body as the legs extend below the body. In some embodiments, the plurality of flexible legs comprises at least one pair of legs, wherein the pair of legs comprises a first leg and a second leg that extend away from and below the body in opposite directions. In some embodiments, the pair of legs is connected by a crossbar connected to the body. In some embodiments, the crossbar is connected to the body of the device through a flexible member. In some embodiments, the flexible member is a hinge. In some embodiments, the device comprises two pairs of legs, wherein each pair of leg is positioned to opposite sides of the body. In some embodiments, the legs are attached to the body through a bottom surface of the body. In some embodiments, the legs are attached to the body through a sidewall of the body. In some embodiments, the legs comprise a metal, metal alloy, ceramic, silicon, or a non-polymeric material. In some embodiments, the legs comprise an elastomeric coating or a non-elastomeric polymer coating. In some embodiments, the coating is bioinert. In some embodiments, the coating is a silicone, a urethane polymer, a poly(p-xylylene) polymer, or a polyimide. In some embodiments, at least one of the legs comprises an outer surface coated with the elastomeric coating or the non-elastomeric polymer coating and an inner surface comprising at least one electrode that is not coated with the elastomeric coating or the non-elastomeric polymer coating. In some embodiments, the body comprises a bottom surface, and the two or more electrodes are terminate on the bottom of the body. In some embodiments, the two or more electrodes are positioned on the clip. In some embodiments, the clip comprises a plurality of flexible legs that extend below the body, and the two or more electrodes are positioned on the flexible legs.

In some embodiments of a method of implanting the medical device in a subject, the body comprises a housing. In some embodiments, the housing comprises a bioinert material. In some embodiments, the housing comprises the bioinert material, and wherein the bioinert material of the housing comprises titanium or a ceramic.

In some embodiments of a method of implanting the medical device in a subject, the body comprises an integrated circuit electrically connected to the ultrasonic transducer and the two or more electrodes. In some embodiments, the integrated circuit comprises an energy storage circuit comprising a capacitor. In some embodiments, the body is about 5 mm or less in length in the longest dimension.

Further described herein is an implantable medical device, comprising: (a) two or more ultrasonic transducers configured to receive ultrasonic waves that power the device and emit an ultrasonic backscatter; (b) an integrated circuit comprising an energy storage circuit comprising a capacitor, wherein the integrated circuit is electrically connected to the first ultrasonic transducer and the second ultrasonic transducer; and (c) one or more of (i) a sensor configured to measure a physiological condition, (ii) two or more electrodes configured to be in electrical communication with a tissue and emit an electrical pulse to the tissue, or (iii) two or more electrodes configured to be in electrical communication with a tissue and detect an electrophysiological signal from the tissue; wherein the sensor or the two or more electrodes are electrically connected to the integrated circuit. In some embodiments, the two or more ultrasonic transducers comprise a first ultrasonic transducer comprising a first polarization axis and a second ultrasonic transducer comprising a second polarization axis, wherein the second ultrasonic transducer is positioned so that the second polarization axis is orthogonal to the first polarization axis, and wherein the first ultrasonic transducer and the second ultrasonic transducer are configured to receive the ultrasonic waves that power the device and emit the ultrasonic backscatter.

In some embodiments, the implantable device comprises the sensor configured to measure a physiological condition. In some embodiments, the sensor is a temperature sensor, a pH sensor, a pressure sensor, a strain sensor, a pulse sensor, a blood pressure sensor, an oxygen meter, a glucose meter, an impedance meter, or is configured to measure an analyte concentration.

In some embodiments, the implantable device comprises the two or more electrodes configured to be in electrical communication with a tissue and emit an electrical pulse to the tissue. In some embodiments, the implantable device comprises the two or more electrodes configured to be in electrical communication with a tissue and detect an electrophysiological signal from the tissue. In some embodiments, the electrophysiological signal is a neural signal. In some embodiments, the ultrasonic backscatter encodes information related to the measured physiological condition, the emitted electrical pulse, or the detected electrophysiological signal.

In some embodiments, the first ultrasonic transducer and the second ultrasonic transducer are electrically connected to the integrated circuit in parallel. In some embodiments, the first ultrasonic transducer, the second ultrasonic transducer, and the integrated circuit are contained within a body, the device further comprising a clip configured to at least partially surround a filamentous tissue. In some embodiments, the filamentous tissue comprises a nerve. In some embodiments, the filamentous tissue comprises a nerve attached to a blood vessel. In some embodiments, the clip comprises a plurality of flexible legs that extend below the body.

In some embodiments of any of the implantable medical devices described above, the implantable medical device does not comprise a battery.

In some embodiments of any of the implantable medical devices described above, the implantable medical device does not comprise a radiofrequency communication system.

In some embodiments of any of the implantable medical devices described above, the implanted medical device does not comprise an electrical lead that extends from the body of the device without terminating on a leg of a clip.

Further provided herein, a system comprises any one of the implantable medical devices described above, and an interrogator comprising one or more ultrasonic transducers configured to transmit ultrasonic waves to the implantable medical device, wherein the ultrasonic waves power the implantable medical device. In some embodiments, the interrogator is configured to be worn externally. In some embodiments, the interrogator is configured to receive ultrasonic backscatter emitted by the implantable device, wherein the ultrasonic backscatter encodes data. In some embodiments, the interrogator is configured to analyze the data or transmit the data to a computer system. In some embodiments, the ultrasonic waves transmitted by the interrogator encode instructions for operating the implantable device.

Also described herein is a method of treating incontinence in a subject, comprising: converting energy from ultrasonic waves into electrical energy that powers a fully implanted medical device in the subject, the device comprising two or more electrodes in electrical communication with a tibial nerve or a branch thereof, a pudendal nerve or a branch thereof, or a sacral nerve or a branch thereof of the subject; and electrically stimulating the tibial nerve or the branch thereof, the pudendal nerve or the branch thereof, or the sacral nerve or the branch thereof, of the subject using the fully implanted medical device. In some embodiments, the tibial nerve or the branch thereof, the pudendal nerve or the branch thereof, or the sacral nerve or the branch thereof is stimulated by the fully implanted medical device in response to a trigger signal encoded in the ultrasonic waves. In some embodiments, electrically stimulating the tibial nerve or the branch thereof, the pudendal nerve or the branch thereof, or the sacral nerve or the branch thereof comprises emitting a plurality of current pulses to the tibial nerve or the branch thereof, the pudendal nerve or the branch thereof, or the sacral nerve or the branch thereof. In some embodiments, electrically stimulating the tibial nerve or the branch thereof, the pudendal nerve or the branch thereof, or the sacral nerve or the branch thereof, comprises emitting a plurality of voltage pulses to the tibial nerve or the branch thereof, the pudendal nerve or the branch thereof, or the sacral nerve or the branch thereof.

In some embodiments of treating incontinence in a subject, the plurality or current pulses or the plurality of voltage pulses are emitted at a constant frequency. In some embodiments, the frequency of the plurality of current pulses or the plurality of voltage pulses is between about 1 Hz and about 50 Hz. In some embodiments, the method comprises transmitting the ultrasonic waves to the implanted medical device using a interrogator comprising one or more ultrasonic transducers. In some embodiments, the ultrasonic waves encode instructions for operating the implantable device.

In some embodiments, the method comprises emitting an ultrasonic backscatter that encodes data. In some embodiments, the data comprises a stimulation status that indicates whether the implantable device emitted an electrical pulse or what parameters were used to emit the electrical pulse. In some embodiments, the method comprises receiving the ultrasonic backscatter. In some embodiments, the method comprises analyzing the data encoded by the ultrasonic backscatter.

In some embodiments of treating incontinence, the interrogator is an externally worn device. In some embodiments, the interrogator contacts the skin of the subject. In some embodiments, the interrogator is operated using a handheld device. In some embodiments, the handheld device is wirelessly connected to the interrogator.

In some embodiments of treating incontinence, the method comprises implanting the medical device in the subject to contact the two or more electrodes to the tibial nerve or the branch thereof, the pudendal nerve or the branch thereof, or the sacral nerve or the branch thereof.

In some embodiments of treating incontinence, the two or more electrodes are in electrical communication with the tibial nerve or the branch thereof. In some embodiments, the interrogator is attached to the ankle of the subject.

In some embodiments of treating incontinence, the two or more electrodes are in electrical communication with the sacral nerve or the branch thereof. In some embodiments, the interrogator is attached the hip, abdomen, lower back, buttocks, or upper leg of the patient.

In some embodiments of treating incontinence, the incontinence is an overactive bladder, an underactive bladder, urinary incontinence, or fecal incontinence.

In some embodiments of treating incontinence, the subject is a human.

In some embodiments of treating incontinence, the implantable device is the implantable medical device is any one of the implantable medical devices described above.

The body further includes an integrated circuit that has a power circuit, which includes a capacitor.

Figure 5:
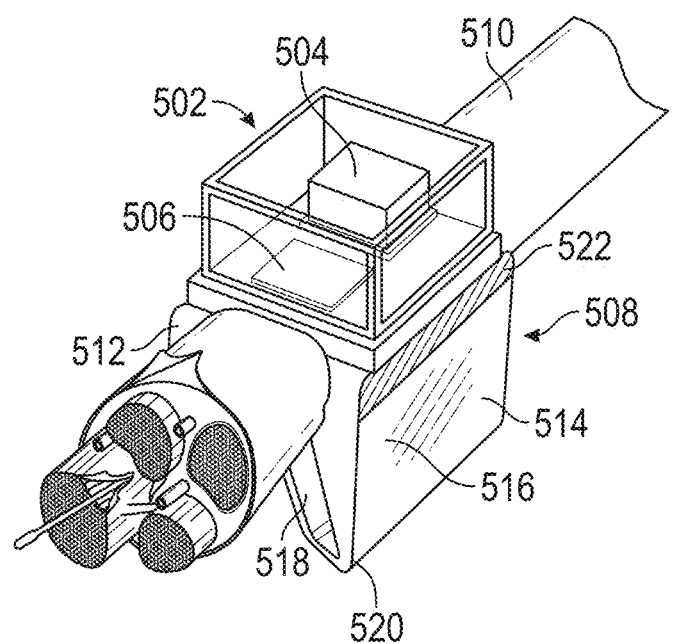

FIG. 5 shows an exemplary implantable device with a body attached to a clip. The body includes an ultrasonic transducer and an integrated circuit, which are electrically connected to electrodes that are in electrical communication with a nerve. The clip holds the body to the nerve and the electrodes in position to electrically stimulate or detect an electrophysiological pulse from a nerve.

Figure 6:
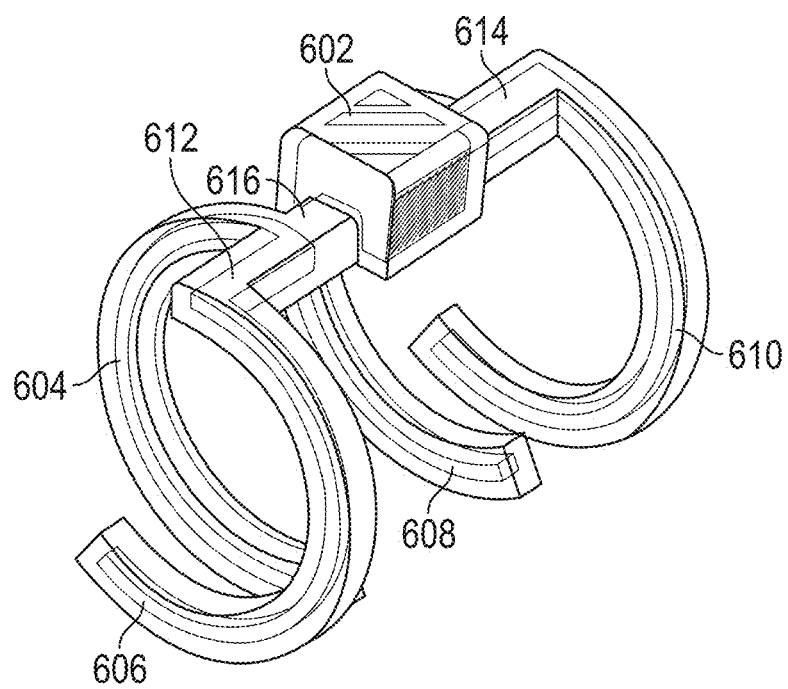

FIG. 6 shows another example of an implantable device that includes a body with a housing that encloses an ultrasonic transduce and an integrated circuit. The body is attached to a clip that includes legs configured to at least partially surround a nerve and position electrodes in electrical communication with the nerve.

Figure 7:
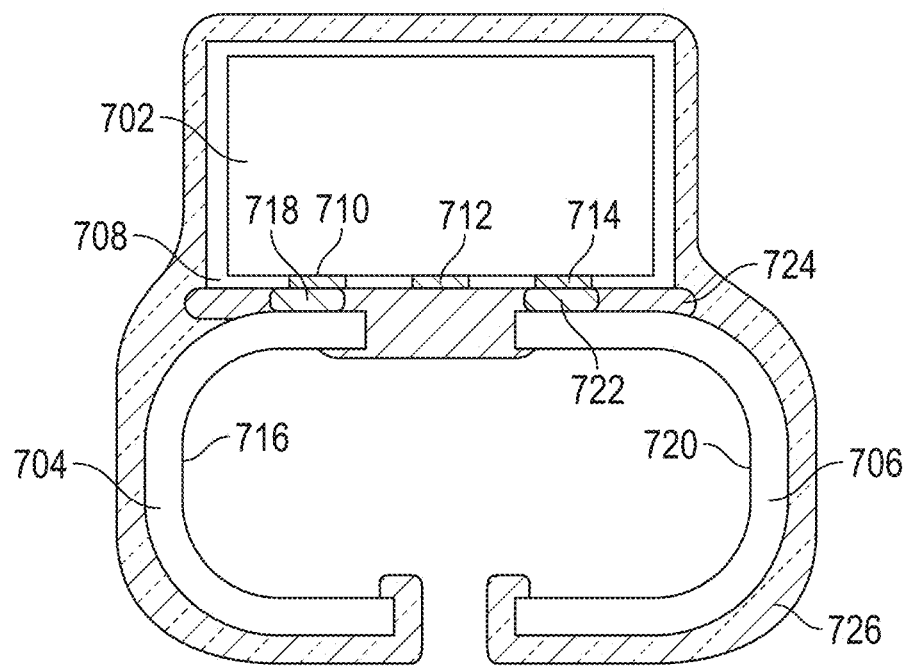

FIG. 7 shows a side view of another embodiment of an implantable device with a body attached to a clip having a plurality of legs. The clip is attached to the body underneath the bottom surface of the body. The legs are coated with a coating (which may be an elastomeric coating or a non-elastomeric polymer coating) on the outer surface of the legs, but are uncoated on the inner surface of the legs. The electrodes are uncoated and positioned on the inner surface of the legs.

Figures 8A, 8B:
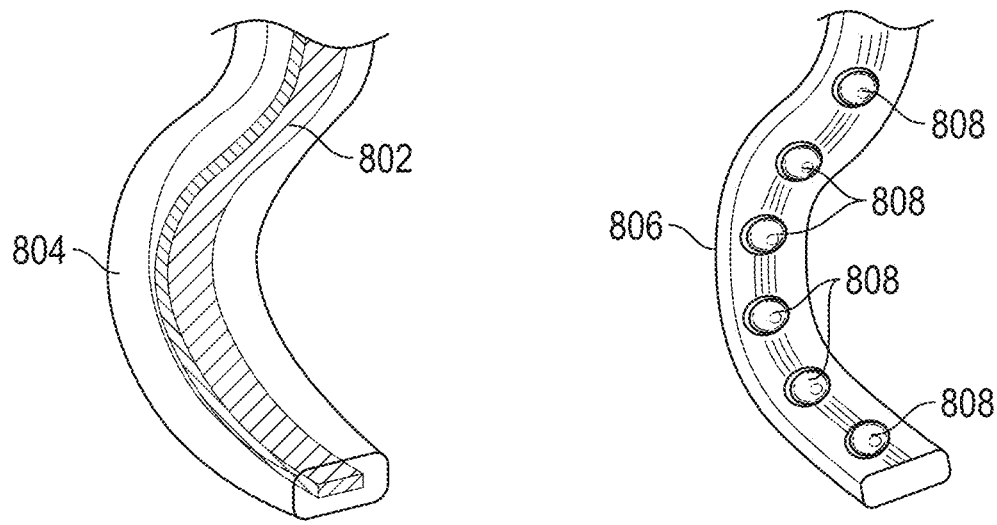

FIG. 8A and FIG. 8B illustrate two exemplary configurations of legs having electrodes positioned on the legs. In FIG. 8A, the leg includes a single electrode that is positioned along the inner surface of the leg. In FIG. 8B, the leg includes a plurality of electrodes that terminate at different positions along the inner surface of the leg.

Figure 9A:
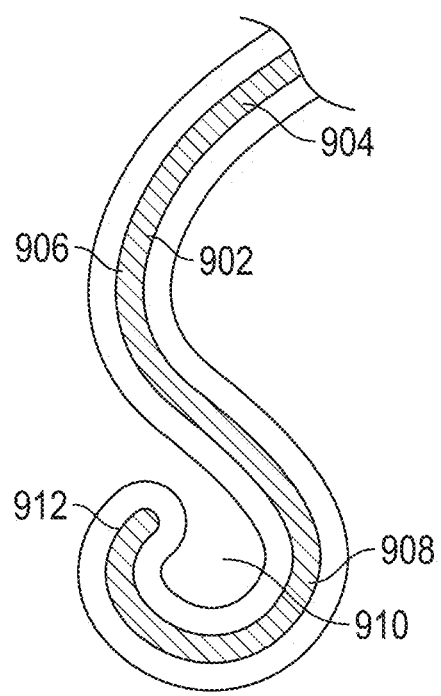
Figure 9B:
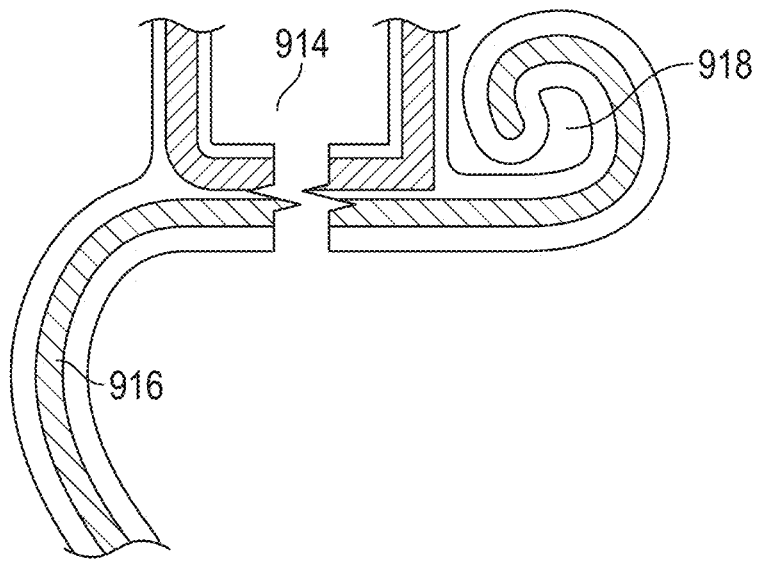

FIG. 9A shows one embodiment of a leg with a hook at the terminus of the leg. FIG. 9B shows an embodiment of an implantable device with a hook proximal to the body of the device. The hook on the device in FIG. 9B is connected to a leg on the opposite side of the body, and maneuvering the hook allows the leg to be flexed outwardly.

Figure 10:
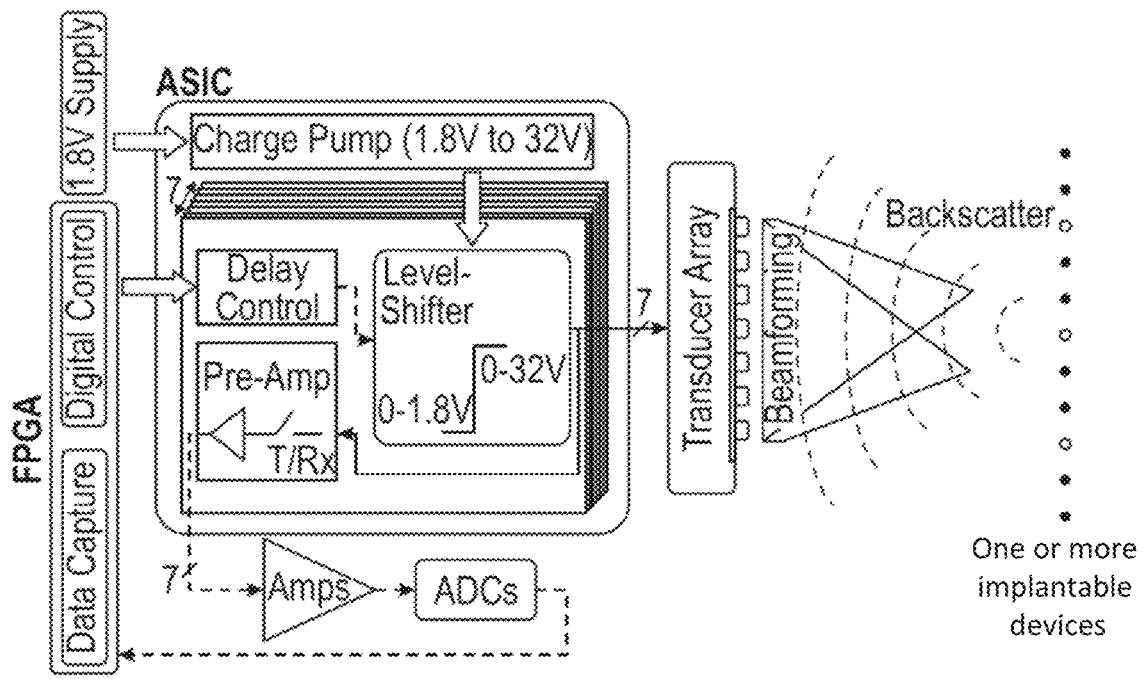

FIG. 10 shows an exemplary interrogator that can be used with the implantable device.

Figure 11:
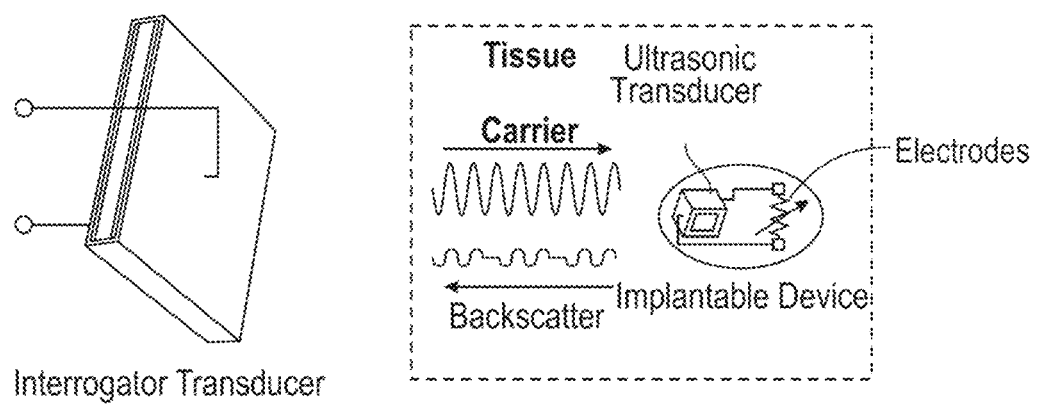

FIG. 11 shows an interrogator in communication with an implantable device. The interrogator can transmit ultrasonic waves, which can encode a trigger signal. The implantable device emits an ultrasonic backscatter, which can be modulated by the implantable device to encode information.

Figure 12:
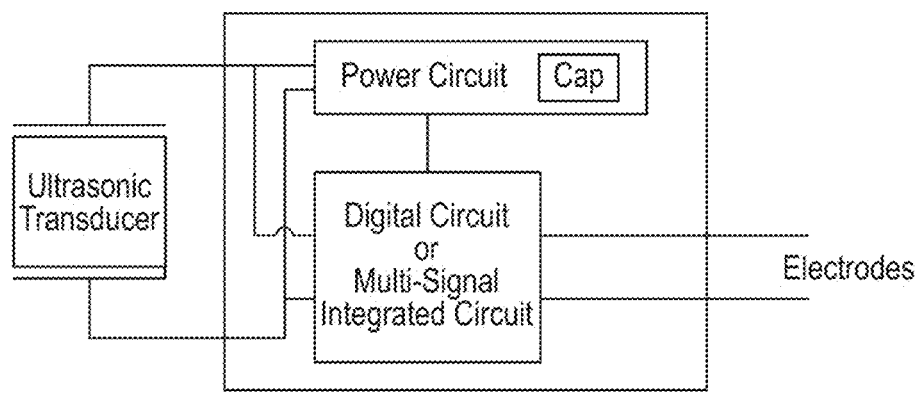

FIG. 12 shows a schematic of one embodiment of an implantable device showing the ultrasonic transducer and electrodes electrically connected to an integrated circuit. The integrated circuit includes a power circuit, which includes a capacitor that can store electrical energy from the ultrasonic transducer. The integrated circuit further includes a digital circuit or a multi-signal integrated circuit, which can operate the power circuit and modulate an electrical current flowing through the ultrasonic transducer to encode information.

Figure 13A:
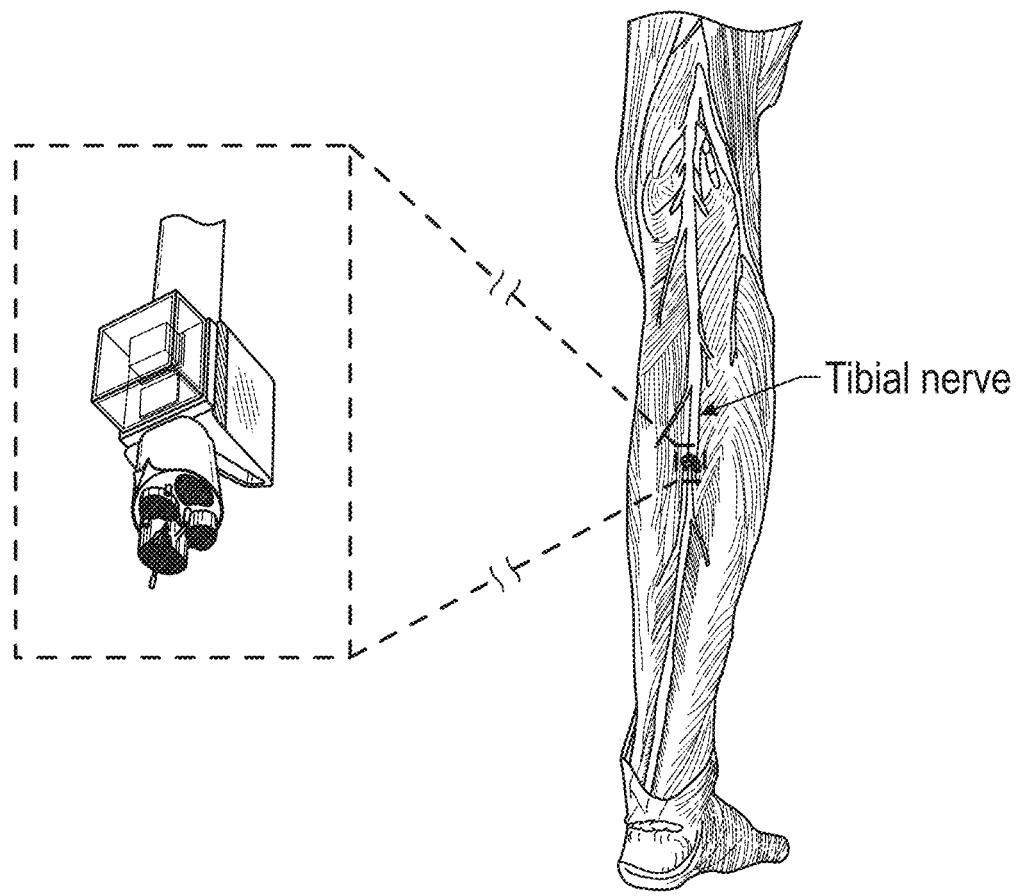
Figure 13B:
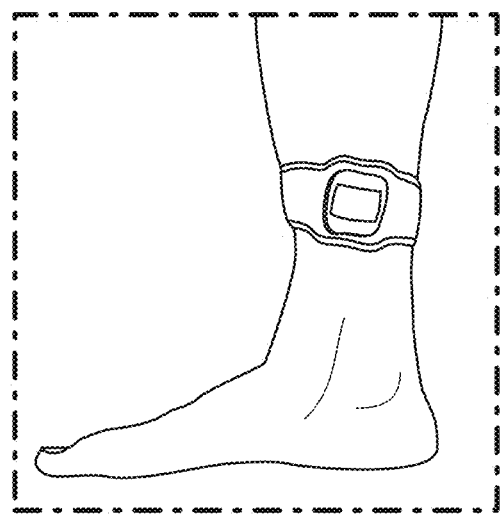

FIG. 13A shows an implantable device with a body and a clip fully implanted in a subject, wherein the clip attaches the implantable device to the tibial nerve. FIG. 13B shows an interrogator worn by a subject that can communicate with the implantable device in electrical communication with the tibial nerve.

Figure 14:
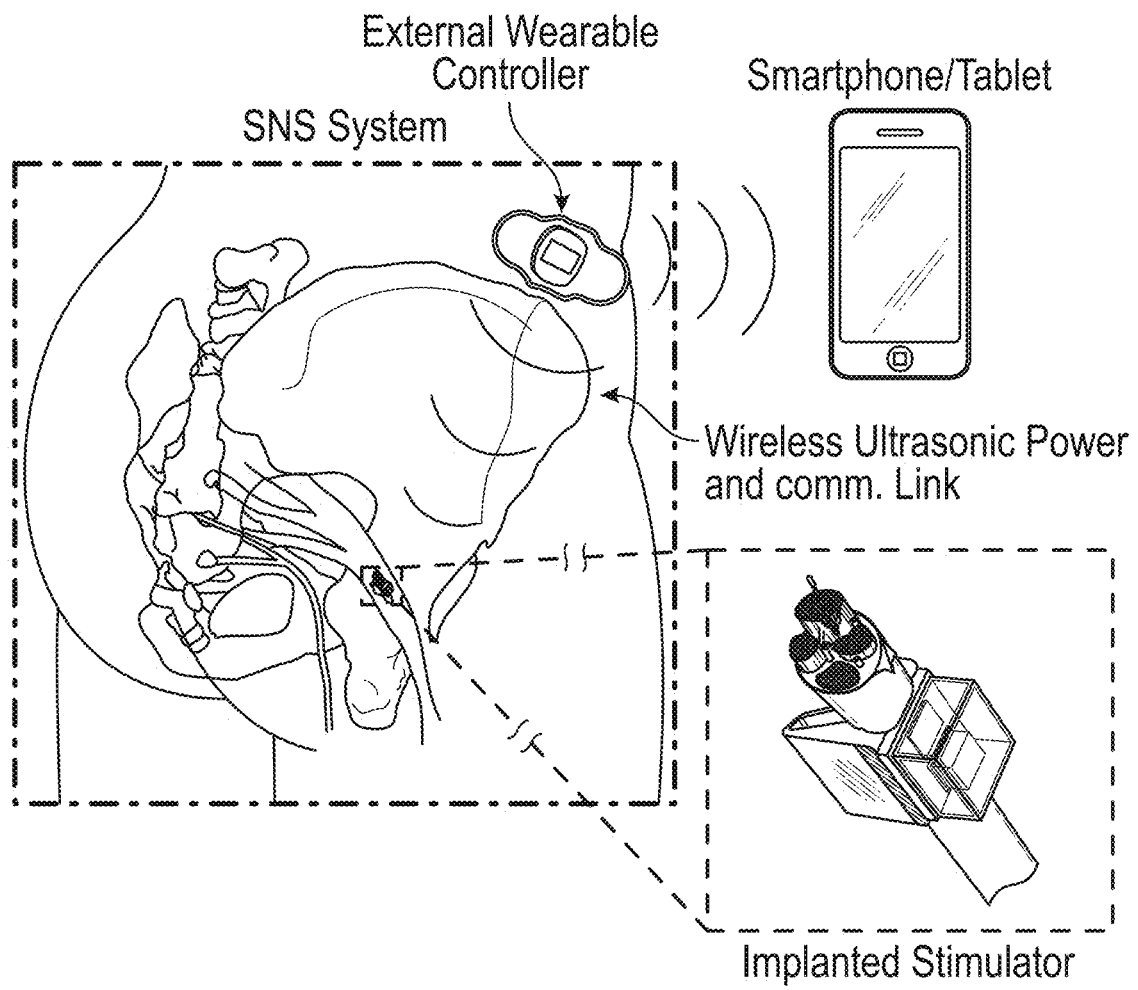

FIG. 14 shows a system that includes an implantable device clipped to a sacral nerve and an interrogator being used for sacral nerve stimulation (SNS). The implantable device includes a body having an ultrasonic transducer, electrodes, and a clip. The interrogator is optionally controlled by a mobile device, such as a smartphone or tablet.

DETAILED DESCRIPTION

Small, implantable devices that can detect electrophysiological signals or a physiological condition, or emit electrical pulse to a nerve, are described herein. The implantable devices are powered by ultrasonic waves emitted by an external interrogator, which are received by an ultrasonic transducer on the implantable device and converted into electrical energy. The ultrasonic waves emitted by the interrogator can further encode instructions for operating the implantable device, which are received by the ultrasonic transducer on the implantable device. The ultrasonic waves transmitted by the external transducer can encode, for example, a trigger signal that can signal the implantable device to emit an electrical pulse. In some embodiments, the implantable device emits ultrasonic backscatter waves, which may be received by the interrogator or other external ultrasonic receiver. The ultrasonic backscatter waves can encode data, such as data related to an electrical pulse (e.g., neural activity) detected by the implantable device, a measured physiological condition, information related to an emitted electrical pulse, or information related to the status of the implantable medical device.

The implantable device can include electrodes for stimulating nerves or detecting neural activity. Because the implantable devices can be implanted in mobile patients, there is a need to ensure the electrodes of the implantable device remain in electrical communication with the target nerve, as movement of the patient can cause shifting of internal tissues. As further described herein, an implantable device can include two or more electrodes, which can be configured to detect an electrophysiological signal or emit an electrical pulse, and a clip that is configured to at least partially surround a nerve and position the two or electrodes in electrical communication with the nerve. In some locations of the body, the target nerve may be attached to another filamentous tissue, such as a blood vessel. Accordingly, in some embodiments, the clip can be configured to at least partially surround the filamentous tissue or blood vessel. By using the clip to position and retain the electrodes in place, there is no need to suture the implantable device to tissue, which facilitates implantation and avoids surrounding tissue damage. For example, the implantable device can now be laparoscopically implanted while ensuring the electrodes are correctly position during use.

Since the implantable device can move relative to the external interrogator, for example due to movement of the target nerve or repositioning of the external interrogator, an implantable device with a single ultrasonic transducer may have a weakened connection to the interrogator if the polarization axis of the ultrasonic transducer of the implantable device becomes unaligned with the polarization axis of the one or more ultrasonic transducers of the interrogator. Accordingly, as further described herein, an implantable device can include two or more ultrasonic transducers with non-parallel polarization axes. For example, in some embodiments, there is an implantable device with a first ultrasonic transducer comprising a first polarization axis and a second ultrasonic transducer comprising second polarization axis, wherein the second ultrasonic transducer is positioned so that the second polarization axis is orthogonal to the first polarization axis. In this configuration, ultrasonic waves emitted by the external transducer can be received by the implantable device positioned in different orientations to allow for continued powering of the implantable device.

The implantable devices described herein may be used to stimulate a nerve to treat a medical condition. Because the implantable devices are small, they can be implanted in a subject with limited invasiveness. Additionally, the implantable device can target nerves that are not practically targeted with larger devices and without leads implanted in the body that are connected externally. For example, the implantable devices may be used to treat incontinence in a subject, for example by electrically stimulating a tibial nerve, a pudendal nerve, or a sacral nerve, or a branch thereof using the fully implanted medical device described herein.

DEFINITIONS

As used herein, the singular forms "a," "an," and "the" include the plural reference unless the context clearly dictates otherwise.

Reference to "about" or "approximately" a value or parameter herein includes (and describes) variations that are directed to that value or parameter per se. For example, description referring to "about X" includes description of "X."

It is understood that aspects and variations of the invention described herein include "consisting" and/or "consisting essentially of" aspects and variations.

The term "subject" and "patient" are used interchangeably herein to refer to a vertebrate animal.

The terms "treat," "treating," and "treatment" are used synonymously herein to refer to any action providing a benefit to a subject afflicted with a disease state or condition, including improvement in the condition through lessening, inhibition, suppression, or elimination of at least one symptom, delay in progression of the disease or condition, delay in recurrence of the disease or condition, or inhibition of the disease or condition.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

Implantable Device

The implantable device includes a body, which contains one or more ultrasonic transducers and an integrated circuit that operates the device. The ultrasonic transducer receives ultrasonic waves, and converts the received ultrasonic waves into an electrical energy that powers the device. The body of the device can include or be connected to two or more electrodes or a sensor, which are in electric communication with the ultrasonic transducer (e.g., through the integrated circuit). In some embodiments, an electric current that flows through the ultrasonic transducer can be modulated to encode information in ultrasonic backscatter waves emitted by the ultrasonic transducer. The information encoded in the ultrasonic backscatter waves may include, for example, data related to a physiological condition detected by the sensor, an electrophysiological signal detected by the electrodes, a status of the device (for example, a status confirming the device is receiving signals encoded in ultrasonic waves, confirming operation of the integrated circuit, or confirming that the device is being powered), or information related to an electrical pulse emitted by the implantable device. In some embodiments, the implantable device comprises a clip attached to the body that is configured to at least partially surround a nerve and position the two or more electrodes in electrical communication with the nerve. In some embodiments, the implantable device comprises a first ultrasonic transducer comprising a first polarization axis and a second ultrasonic transducer comprising second polarization axis, wherein the second ultrasonic transducer is positioned so that the second polarization axis is orthogonal to the first polarization axis, and wherein the first ultrasonic transducer and the second ultrasonic transducer are configured to receive ultrasonic waves that power the device and emit an ultrasonic backscatter.

In some embodiments, the implantable device is implanted in a subject. The subject can be for example, a mammal. In some embodiments, the subject is a human, dog, cat, horse, cow, pig, sheep, goat, monkey, or a rodent (such as a rat or mouse).

Body of the Implantable Device

The body of the implantable device includes one or more ultrasonic transducers, and a sensor and/or an electrode pair. The electrode pair can be configured to detect an electrophysiological signal or emit an electrical pulse. Exemplary implantable devices that can detect an electrophysiological signal and encode information related to the detected electrophysiological signal are described in WO 2018/009910 A2. Exemplary implantable devices that can be operated using ultrasonic waves to emit an electrical pulse are described in WO 2018/009912 A2. The sensor may be, for example, sensor the can detect or measure a physiological condition (such as temperature sensor, an oxygen sensor, a pH sensor, a strain sensor, a pressure sensor, an impedance sensor, or a sensor that can detect a concentration of an analyte). Exemplary implantable devices that are powered by ultrasonic waves and can emit an ultrasonic backscatter encoding a detected physiological condition are described in WO 2018/009905 A2 and WO 2018/009911 A2. In some embodiments, the implantable device comprises both a sensor and an electrode pair. In some embodiments, an integrated circuit is included in the implantable device, which can electrically connect and communicate between the electrodes or sensor and the ultrasonic transducer. The integrated circuit can include a modulation circuit, which modulates an electrical current flowing through the one or more ultrasonic transducers to encode data in the electrical current. The modulated electrical current affects ultrasonic backscatter waves emitted by the ultrasonic transducer, and the ultrasonic backscatter waves encode the data.

Figure 1:
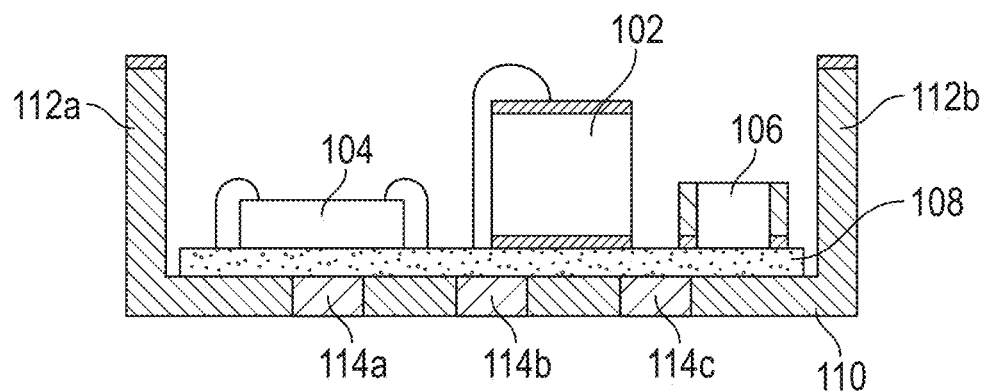
FIG. 1 shows a side view of a body of an implantable device. The body includes an ultrasonic transducer electrically connected to an integrated circuit that includes a power circuit with a capacitor. The body further includes a bottom surface comprising feedthroughs, which allow the integrated circuit to electrically connect with electrodes positioned elsewhere on the device.

FIG. 1 shows a side view of an exemplary implantable device body with an ultrasonic transducer 102 and an integrated circuit 104. In the illustrated embodiment, the integrated circuit 104 includes a power circuit that includes a capacitor 106. The capacitor can temporarily store electrical energy converted from ultrasonic energy by the ultrasonic transducer, and can be operated by the integrated circuit 104 to store or release energy. The ultrasonic transducer 102, integrated circuit 104, and the capacitor 106 are mounted on a backplate 108, which may be a printed circuit board. The base 108 is set in a housing, which includes a bottom surface 110 and sidewalls 112a and 112b. The housing can further include a top (not shown) that seals the body components in the housing. The bottom surface 110 may include one or more feedthroughs 114a, 114b, and 114c that electrically connect the backplate and/or integrated circuit to one or more electrodes. The one or more electrodes may be located, for example, underneath the bottom surface 110 of the housing, or may be located on a clip as described herein. In this configuration, the electrodes can be in electrical communication with the nerve, and the components of the body are positioned above the nerve when the implantable device is implanted and attached to the nerve, for example using the clip as discussed herein. The ultrasonic transducer 102 is electrically connected to the integrated circuit 104, and the integrated circuit 104 is electrically connected to the electrodes via the feedthroughs, thereby electrically connecting the ultrasonic transducer 102 to the electrodes.

Figure 2:
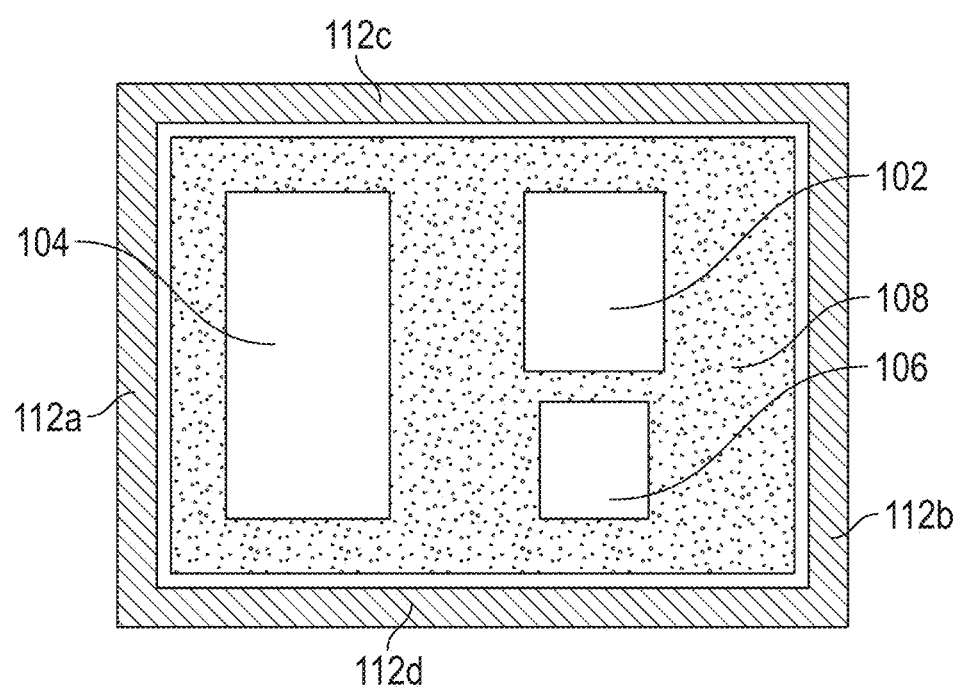
FIG. 2 shows a top view of a body of an implantable device, including an ultrasonic transducer, an integrated circuit, and a capacitor.

FIG. 2 illustrates a top view of the body similar to the one shown in FIG. 1, again without the top of the housing. The housing is shown with four sidewalls 112a, 112b, 112c, and 112d, although it is understood that the housing can be of any suitable shape (e.g., with three, four, five, six or more sidewalls, or with a single curved sidewall in a round or oval shape).

Figure 3:
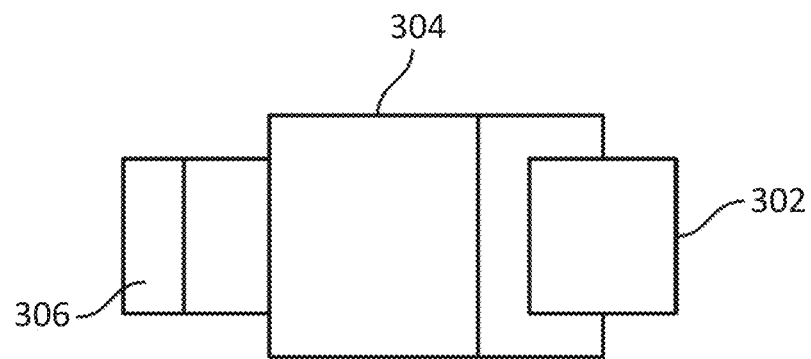
FIG. 3 shows an exemplary implantable device that includes an ultrasonic transducer, an integrated circuit and a sensor, which can be configured to measure a physiological condition.

FIG. 3 illustrates a schematic of an exemplary implantable device with an ultrasonic transducer 302, and integrated circuit 304, and a sensor 306 (such as sensor that can detect a temperature, pressure, strain, analyte concentration, oxygen, or pH). The ultrasonic transducer 302 is electrically connected to the integrated circuit 304, which his electrically connected to the sensor 306. Although the illustrated embodiment is shown with an integrated circuit, it is also conceived that the sensor can be directly connected to the ultrasonic transducer. Further, as discussed herein, one or more sensor can be included on an implantable device further having electrodes configured to detect and/or emit an electrical pulse.

The ultrasonic transducer is configured to receive ultrasonic waves and convert energy from the ultrasonic waves into an electrical energy. The electrical energy is transmitted to the integrated circuit to power the device. The implantable device can also operate to receive or transmit data through ultrasonic waves. Ultrasonic waves received by the implantable device (for example, those transmitted by the interrogator) can encode instructions for operating the implantable device. The instructions may include, for example, a trigger signal that instructs the implantable device to emit an electrical pulse through the electrodes. The trigger signal may include, for example, information relating to when the electrical pulse should be emitted, a pulse frequency, a pulse power or voltage, a pulse shape, and/or a pulse duration The implantable device can also operate to transmit data, which can be received by the interrogator. The ultrasonic transducer(s) on the implantable device receive ultrasonic waves and emit an ultrasonic backscatter, which can encode data transmitted by the implantable device. Current flows through the ultrasonic transducer, which can be modulated to encode the data. The current may be modulated directly, for example by passing the current through a sensor that modulates the current, or indirectly, for example by modulating the current using a modulation circuit based on a detected physiological condition or an electrophysiological pulse. In some embodiments, the data encoded in the ultrasonic waves includes data unrelated to a detected physiological condition or electrophysiological pules detected by the implantable device. For example, the data can include information related to the status of the implantable device or a confirmation signal that confirms an electrical pulse was emitted, and optionally the power, frequency, voltage, duration, or other information related to an emitted electrical pulse.

In some embodiments, the body includes a housing, which can include a base, one or more sidewalls, and a top. The housing can enclose the one or more ultrasonic transducers and the integrated circuit. The hosing may be sealed closed (for example by soldering or laser welding) to prevent interstitial fluid from coming in contact with the ultrasonic transducer(s) and/or the integrated circuit. The electrodes that are configured to be in electrical communication with the nerve are not enclosed by the housing. The housing is preferably made from a bioinert material, such as a bioinert metal (e.g., steel or titanium) or a bioinert ceramic (e.g., titania or alumina). The housing (or the top of the housing) may be thin to allow ultrasonic waves to penetrate through the housing. In some embodiments, the thickness of the housing is about 100 micrometers (µm) or less in thickness, such as about 75 µm or less, about 50 µm or less, about 25 µm or less, or about 10 µm or less. In some embodiments, the thickness of the housing is about 5 µm to about 10 µm, about 10 µm to about 25 µm, about 25 µm to about 50 µm, about 50 µm to about 75 µm, or about 75 µm to about 100 µm in thickness.

In some embodiments, the body comprises a material, such as a polymer, within the housing. The material can fill empty space within the housing to reduce acoustic impedance mismatch between the tissue outside of the housing and within the housing. Accordingly, the body of the device is preferably void of air or vacuum.

The body of the implantable device is relatively small, which allows for comfortable and long-term implantation while limiting tissue inflammation that is often associated with implantable devices. In some embodiments, the longest dimension of the body of the device is about 5 mm or less, about 4 mm or less, about 3 mm or less, about 2 mm or less, about 1 mm or less, about 0.5 mm or less, about 0.3 mm or less, about 0.1 mm or less in length. In some embodiments, the longest dimension of the body of the device is about 0.05 mm or longer, about 0.1 mm or longer, about 0.3 mm or longer, about 0.5 mm or longer, about 1 mm or longer, about 2 mm or longer, or about 3 mm or longer in the longest dimension of the device. In some embodiments, the longest dimension of the body of the device is about 0.04 mm to about 5 mm in length, about 0.05 mm to about 4 mm in length, about 0.07 mm to about 3 mm in length, about 0.08 mm to about 3 mm in length, or about 1 mm to about 2 mm in length.

In some embodiments, the body of the implantable device has a volume of about 5 $mm^3$ or less (such as about 4 $mm^3$ or less, 3 $mm^3$ or less, 2 $mm^3$ or less, or 1 $mm^3$ or less). In some embodiments, the body of the implantable device has a volume of about 0.5 $mm^3$ to about 5 $mm^3$, about 1 $mm^3$ to about 5 $mm^3$, about 2 $mm^3$ to about 5 $mm^3$, about 3 $mm^3$ to about 5 $mm^3$, or about 4 $mm^3$ to about 5 $mm^3$. The small size of the implantable device allows for laparoscopic implantation of the device, thereby minimizing tissue damage when implanting the device.

The implantable device includes one or more ultrasonic transducers, such as one, two, or three or more ultrasonic transducers. In some embodiments, the implantable device includes a first ultrasonic transducer having a first polarization axis and a second ultrasonic transducer having a second polarization axis, wherein the second ultrasonic transducer is positioned so that the second polarization axis is orthogonal to the first polarization axis, and wherein the first ultrasonic transducer and the second ultrasonic transducer are configured to receive ultrasonic waves that power the device and emit an ultrasonic backscatter. In some embodiments, the implantable medical device includes a first ultrasonic transducer having a first polarization axis, a second ultrasonic transducer having a second polarization axis, and a third ultrasonic transducer having a third polarization axis, wherein the second ultrasonic transducer is positioned so that the second polarization axis is orthogonal to the first polarization axis and the third polarization axis, wherein the third ultrasonic transducer is positioned so that the third polarization axis is orthogonal to the first polarization and the second polarization axis, and wherein the first ultrasonic transducer and the second ultrasonic transducer are configured to receive ultrasonic waves that power the device and emit an ultrasonic backscatter. An implantable device with one, two, or three or more ultrasonic transducers may further include a sensor or two or more electrodes configured to be in electrical communication with a tissue, such as a nerve. Optionally, the implantable device further includes an integrated circuit.

Figure 4:
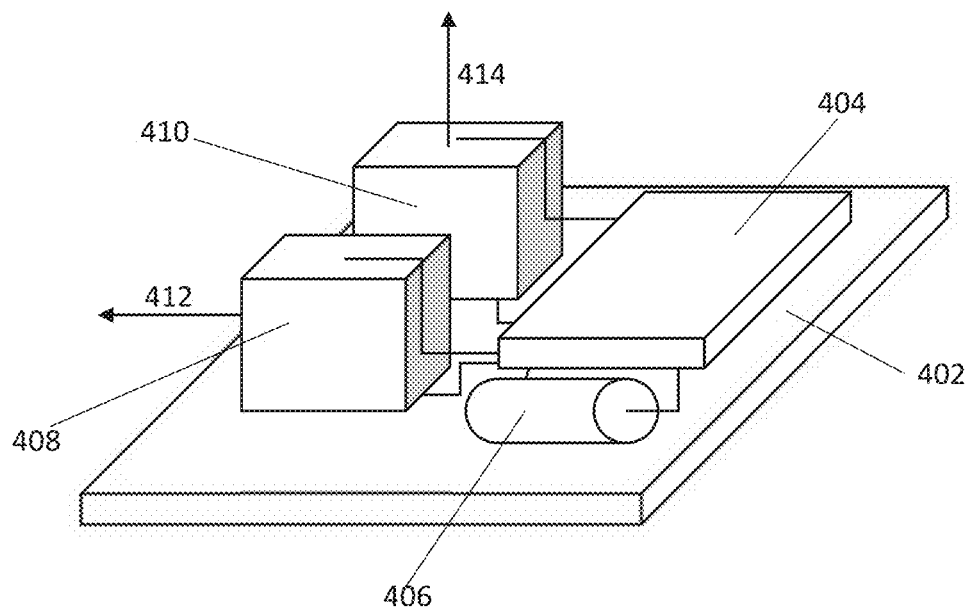
FIG. 4 shows a body of an implantable device that includes two orthogonally positioned ultrasonic transducers.

FIG. 4 shows a body of a device that includes two orthogonally positioned ultrasonic transducers. The body includes a backplate 402, such as a printed circuit board, and an integrated circuit 404, which a power circuit that includes a capacitor 406. The body further includes a first ultrasonic transducer 408 electrically connected to the integrated circuit 404, and a second ultrasonic transducer 410 electrically connected to the integrated circuit 404. The first ultrasonic transducer 408 includes a first polarization axis 412, and the second ultrasonic transducer 410 includes a second polarization axis 414. The first ultrasonic transducer 408 and the second ultrasonic transducer are positioned such that the first polarization axis 412 is orthogonal to the second polarization axis 414. A housing (not shown) can enclose and optionally seal the body components. Further, the integrated circuit can be electrically coupled to a sensor or electrodes.

The ultrasonic transducer of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di)fluoride (PVDF), and lead magnesium niobate-lead titanate (PMN-PT).

In some embodiments, the bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. In some embodiments, the bulk piezoelectric transducer is long and narrow, with an aspect ratio of about 3:1:1 or greater, and where the longest dimension is aligned to the direction of the ultrasonic backscatter waves (i.e., the polarization axis). In some embodiments, one dimension of the bulk piezoelectric transducer is equal to one half of the wavelength ($\lambda$) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 μm to about 1000 μm (such as about 40 μm to about 400 μm, about 100 μm to about 250 μm, about 250 μm to about 500 μm, or about 500 μm to about 1000 μm). In some embodiments, the height of the piezoelectric transducer is about 5 mm or less (such as about 4 mm or less, about 3 mm or less, about 2 mm or less, about 1 mm or less, about 500 μm or less, about 400 μm or less, 250 μm or less, about 100 μm or less, or about 40 μm or less). In some embodiments, the height of the piezoelectric transducer is about 20 μm or more (such as about 40 μm or more, about 100 μm or more, about 250 μm or more, about 400 μm or more, about 500 μm or more, about 1 mm or more, about 2 mm or more, about 3 mm or more, or about 4 mm or more) in length.

In some embodiments, the ultrasonic transducer has a length of about 5 mm or less such as about 4 mm or less, about 3 mm or less, about 2 mm or less, about 1 mm or less, about 500 μm or less, about 400 μm or less, 250 μm or less, about 100 μm or less, or about 40 μm or less) in the longest dimension. In some embodiments, the ultrasonic transducer has a length of about 20 μm or more (such as about 40 μm or more, about 100 μm or more, about 250 μm or more, about 400 μm or more, about 500 μm or more, about 1 mm or more, about 2 mm or more, about 3 mm or more, or about 4 mm or more) in the longest dimension.

The ultrasonic transducer is connected two electrodes to allow electrical communication with the integrated circuit. The first electrode is attached to a first face of the transducer and the second electrode is attached to a second face of the transducer, wherein the first face and the second face are opposite sides of the transducer along one dimension. In some embodiments, the electrodes comprise silver, gold, platinum, platinum-black, poly(3,4-ethylenedioxythiophene (PEDOT), a conductive polymer (such as conductive PDMS or polyimide), or nickel. In some embodiments, the axis between the electrodes of the transducer is orthogonal to the motion of the transducer.

In some embodiments, the implantable device includes two or more electrodes in electrical communication with a tissue, such as a nerve. The implantable device can include, for example, a clip as described herein to position and retain the electrodes in electrical communication with the nerve. In some embodiments, an electrical pulse emitted by the implantable device stimulates an action potential in the tissue. In some embodiments, an electrical pulse emitted by the implantable device blocks an action potential in a tissue.

In some embodiments, the implantable device comprises a plurality of electrodes. In some embodiments, the electrodes are paired. Electrode pairs can be formed from two electrodes; thus, an implantable device with three electrodes can have three electrode pairs. The electrophysiological signal can be detected between the electrodes in the electrode pairs, or tissue can be stimulated using any of the electrode pairs. In some embodiments, the implantable device comprises 1, 2, 3, 4, 5, 6, 7, 8, 9, 10 or more, or 15 or more electrode pairs. In some embodiments, the implantable device comprises 2, 3, 5, 6, 7, 8, 9, 10 or more electrodes. In some embodiments, the implantable device includes a multiplexer, which can select the electrodes in the electrode pair to emit the electrical pulse or the electrode pair that detects an electrical pulse.

Two or more electrodes that are electrically connected to the nerve or tissue need not be linearly disposed along the tissue. For example, the electrodes may engage a nerve or other tissue along a transverse axis relative to the nerve, which can emit an electrical pulse in the transverse direction. Two or more electrodes can engage a nerve or other tissue along the transverse axis at any angle, such as directly opposite (i.e., 180°), or less than 180° (such as about 170° or less, about 160° or less, about 150° or less, about 140° or less, about 130° or less, about 120° or less, about 110° or less, about 100° or less, about 90° or less, about 80° or less, about 70° or less, about 60° or less, about 50° or less, about 40° or less, or about 30° or less).

In some embodiments, the electrodes in an electrode pair are separated by about 5 mm or less (such as about 4 mm or less, about 3 mm or less, about 2 mm or less, about 1.5 mm or less, about 1 mm or less, or about 0.5 mm or less). In some embodiments, the electrodes in the electrode pair are separated by about 0.5 mm or more (such as about 1 mm or more, about 1.5 mm or more, about 2 mm or more, about 3 mm or more, or about 4 or more. In some embodiments, the electrodes are separated by about 0.5 mm to about 1 mm, about 1 mm to about 1.5 mm, about 1.5 mm to about 2 mm, about 2 mm to about 3 mm, about 3 mm to about 4 mm, or about 4 mm to about 5 mm.

The electrodes are electrically coupled to the integrated circuit in the body of the implantable device. In some embodiments, the electrodes are positioned or terminate below the body, for example on a face of the base of the body housing opposite the body components (e.g., ultrasonic transducer, integrated circuit, etc.). In some embodiments, the electrodes terminate along a leg of a clip, as detailed herein. In some embodiments, one or more electrodes are exposed along at least a portion of the length of one of the legs.

The electrodes may be electrically coupled to the integrated circuit through one or more feedthroughs in the base of the housing. The feedthroughs may be, for example, a metal (such as a metal comprising silver, copper, gold, platinum, platinum-black, or nickel) sapphire, or a conductive ceramic (for example indium tin oxide (ITO)). The electrodes may be connected to the feedthrough using any suitable means, such as soldering, laser welding, or crimping the feedthrough to the electrodes.

In some embodiments, the implantable device includes one or more sensors. The sensors are configured to detect a physiological condition, such as temperature, oxygen concentration, pH, an analyte (such as glucose), strain, or pressure. Variation in the physiological condition modulates impedance, which in turn modulates current flowing through the ultrasonic transducer on the implantable device. As explained above, this produces ultrasonic backscatter detected by the interrogator; changes in the ultrasonic backscatter waves reflect information about the physiological condition. In some embodiments, the system is configured to detect changes in the physiological system. In some embodiments, the system is configured detect a value or an approximate value of the physiological condition, for example by calibrating the ultrasonic backscatter to known values. The implantable device may comprise one or more (such as 2, 3, 4, 5 or more) sensors, which may detect the same physiological condition or different physiological conditions. In some embodiments, the implantable device comprises 10, 9, 8, 7, 6 or 5 or fewer sensors). For example, in some embodiments, the implantable device comprises a first sensor configured to detect temperature and a second sensor configured to detect oxygen. Changes in both physiological conditions can be encoded in the ultrasonic backscatter waves, which can be deciphered by an external computing system.

The integrated circuit communicates between the ultrasonic transducer and the sensor and/or electrodes. For example, the ultrasonic transducer can receive information encoded in ultrasonic waves and generate an electrical current that encodes the information, which is transmitted to the integrated circuit. The information encoded in the electrical current can include instructions to operate the electrodes and/or sensor, and the integrated circuit can operate the electrodes and/or sensor in accordance with the instructions. The integrated circuit can also receive signals from the sensor and/or electrodes, and can modulate the electrical current flowing through the ultrasonic transducer to encode information related to the signals received from the sensor and electrodes.

In some embodiments, the implantable device emits ultrasonic backscatter that encodes information. The ultrasonic backscatter can be received by the interrogator, for example, and deciphered to determine the encoded information. The information can be encoded using a modulation circuit within the integrated circuit of the implantable device. The modulation circuit can modulate the current flowing through the ultrasonic transducer to encode the information (e.g., information related to a detected electrophysiological pulse or a physiological condition, or information related to the device status). The modulated current flows through the ultrasonic transducer to modulate the ultrasonic backscatter, thereby encoding the information in the ultrasonic backscatter waves. The modulation circuit includes one or more switches, such as an on/off switch or a field-effect transistor (FET). An exemplary FET that can be used with some embodiments of the implantable device is a metal-oxide-semiconductor field-effect transistor (MOSFET). The modulation circuit can alter the impedance of a current flowing through the ultrasonic transducer, and variation in current flowing through the transducer encodes the electrophysiological signal. In some embodiments, information encoded in the ultrasonic backscatter includes a unique identifier for the implantable device. This can be useful, for example, to ensure the interrogator is in communication with the correct implantable device when a plurality of implantable devices is implanted in the subject. In some embodiments, the information encoded in the ultrasonic backscatter includes a verification signal that verifies an electrical pulse was emitted by the implantable device. In some embodiments, the information encoded in the ultrasonic backscatter includes an amount of energy stored or a voltage in the energy storage circuit (or one or more capacitors in the energy storage circuit). In some embodiments, the information encoded in the ultrasonic backscatter includes a detected impedance. Changes in the impedance measurement can identify scarring tissue or degradation of the electrodes over time.

In some embodiments, the modulation circuit is operated by a digital circuit or a mixed-signal integrated circuit, which can actively encode the information in a digitized or analog signal. The digital circuit or mixed-signal integrated circuit may include a memory and one or more circuit blocks, systems, or processors for operating the implantable device. These systems can include, for example, an onboard microcontroller or processor, a finite state machine implementation, or digital circuits capable of executing one or more programs stored on the implant or provided via ultrasonic communication between interrogator and implantable device. In some embodiments, the digital circuit or a mixed-signal integrated circuit includes an analog-to-digital converter (ADC), which can convert analog signal encoded in the ultrasonic waves emitted from the interrogator so that the signal can be processed by the digital circuit or the mixed-signal integrated circuit. The digital circuit or mixed-signal integrated circuit can also operate the power circuit, for example to generate the electrical pulse to stimulate the tissue. In some embodiments, the digital circuit or the mixed-signal integrated circuit receives the trigger signal encoded in the ultrasonic waves transmitted by the interrogator, and operates the power circuit to discharge the electrical pulse in response to the trigger signal.

In some embodiments, the integrated circuit includes a power circuit, which can include an energy storage circuit. The implantable device powered by ultrasonic waves is preferably batteryless, although the energy storage circuit can include one or more capacitors to temporarily store electrical energy. Energy from the ultrasonic waves is converted into a current by the ultrasonic transducer, and can be stored in the energy storage circuit. The energy can be used to operate the implantable device, such as providing power to the digital circuit, the modulation circuit, or one or more amplifiers, or can be used to generate the electrical pulse used to stimulate the tissue. In some embodiments, the power circuit further includes, for example, a rectifier and/or a charge pump.

In some embodiments, the integrated includes a driver circuit, which provides current to one or more sensors and/or electrodes. Optionally, the driver circuit is operated by the digital circuit or mixed-signal integrated circuit if present. In some embodiments, one or more amplifiers are disposed between the driver circuit and the digital circuit. In some embodiments, the integrated includes a front end circuit (such as a CMOS front end), which can receive a signal from the sensor/and or electrodes. The signal received by the front end circuit can be relayed to the digital circuit.

FIG. 12 shows a schematic an embodiment of an implantable device that includes an integrated circuit and electrodes configured to emit an electrical pulse. The implantable device includes a ultrasonic transducer, a power circuit including an energy storage circuit (which can include one or more capacitors ("cap"), a digital circuit or multi-signal integrated circuit, and a pair of electrodes. The ultrasonic transducer is connected to the power circuit, which allows energy from the ultrasonic waves to be stored in the energy storage circuit. The power circuit is connected to the digital circuit or multi-signal integrated circuit so that the digital circuit or multi-signal integrated circuit can operate the power circuit. The digital circuit or multi-signal integrated circuit is also connected to the ultrasonic transducer. When a trigger signal is encoded in ultrasonic waves received by the ultrasonic transducer, the digital circuit or multi-signal integrated circuit can detect the trigger signal. The digital circuit or multi-signal integrated circuit can then operate the power circuit to release energy stored in the energy circuit, thereby emitting an electrical pulse using the electrodes. Optionally, the digital circuit or multi-signal integrated circuit can operate or include a modulation circuit, which can modulate the electrical current flowing through the ultrasonic transducer to encode information, such as information relating to operation of the implantable device or information related to an electrical pulse detected by the electrodes.

Clip for the Implantable Device

In some embodiments, the implantable medical device includes a clip attached to the body that is configured to at least partially surround a nerve to position the two or more electrodes in electrical communication with the nerve. Some nerves in the body may be attached to an adjacent filamentous tissue (e.g., a blood vessel or tendon), and the clip can be configured to at least partially surround the nerve and the filamentous tissue.

The clip holds the implantable device in place on the nerve and/or filamentous tissue. In some embodiments, the clip allows for some rotational movement of the implantable device on the nerve and/or filamentous tissue. In some embodiments, the clip grips the nerve and/or filamentous tissue by exerting an inward pressure on the nerve and/or filamentous tissue. The amount of inward pressure exerted by the clip can be determined based on the size and curvature of the clip, as well as by the spring constant of the clip legs. The inward pressure should be sufficient to hold the implantable device in place while the tissue heals after insertion, but not so high that the epineurium or vascular walls that contact the legs are damaged. In some embodiments, the inward pressure on the nerve or filamentous tissue is about 1 MPa or less (such as about 0.7 MPa or less, about 0.5 MPa or less, or about 0.3 MPa or less). In some embodiments, the inward pressure on the nerve or filamentous tissue is about 0.1 MPa to about 1 MPa (such as about 0.1 MPa to about 0.3 MPa, about 0.3 MPa to about 0.5 MPa, about 0.5 MPa to about 0.7 MPa, or about 0.7 MPa to about 1 MPa).

In some embodiments, the implantable medical device includes a body comprising an ultrasonic transducer configured to receive ultrasonic waves and convert energy from the ultrasonic waves into an electrical energy that powers the device; two or more electrodes in electrical communication with the ultrasonic transducer; and a clip attached to the body that is configured to at least partially surround a nerve (or a nerve and a filamentous tissue attached to the nerve, such as a blood vessel) and position the two or more electrodes in electrical communication with the nerve.

The clip can include a plurality of flexible legs that extend below the body of the implantable device. In some embodiments, the legs are curved. For example, in some embodiments, the legs extend away from the body before curving toward the body as the legs extend below the body. The clip may include pairs of legs, with each leg in the pair extending away from the body in opposite directions. This configuration allows the legs to wrap around the nerve and/or filamentous tissue (or at least partially wrap around the nerve and/or filamentous tissue). The legs in the pair of legs can be connected by a crossbar, which allows the legs to be positioned in a staggered configuration, with one the legs in the pair being positioned closer to the body than the other leg. By staggering the legs at different distances from the body of the device, the legs can extend such that the ends of the legs extend past each other to completely surround the nerve and/or filamentous tissue. In some embodiments, the legs in the pair of the legs and the crossbar are a single piece (e.g., co-extruded or a co-printed) of material, such as a metal, metal alloy, ceramic, silicon, or a non-polymeric material. The legs or the crossbar(s) of the device are connected to the body of the dive. If the implantable device includes two pairs of legs each connected by a crossbar, the crossbars may be attached to the body at opposite ends of the body. The lengths of the crossbars attached to the body can be along the same axis, which can be parallel to the axis of the nerve and/or filamentous tissue.

In some embodiments, the legs or the crossbar(s) of the implantable device are connected to the body of the device through a flexible member, such as a hinge (which may be a spring hinge). The flexibility of the legs and flexible member allows the implantable device to be maneuvered in position on the nerve by flexing the legs of the clip, which can return to their default position to correctly position the electrodes of the device in electrical communication with the nerve.

FIG. 5 shows one example of an implantable device with a clip. The implantable device includes a body 502, which includes an ultrasonic transducer 504 and an integrated circuit 506. The ultrasonic transducer 504 can receive ultrasonic waves from an interrogator, and the ultrasonic transducer converts energy from the ultrasonic waves into an electrical energy that powers the device. The ultrasonic transducer 504 is electrically connected to the integrated circuit 506, which can encode data in an electric current that flows through the ultrasonic transducer 504. The ultrasonic transducer 504 emits an ultrasonic backscatter based on the received current, and the ultrasonic backscatter encodes the data that was encoded in the electric current.

The implantable device includes two or more electrodes that are in electric communication with the ultrasonic transducer 504, for example through the integrated circuit 506. In some configurations, the electrodes are configured to emit an electrical pulse to the nerve, for example by being operated by the integrated circuit 506. Optionally, an electrophysiological pulse can be detected by the electrodes and communicated to the integrated circuit 506, which can modulate an electric current flowing through the ultrasonic transducer 504 based on the detected electrophysiological pulse. The body 502 of the implantable device is attached to a clip 508. The clip is configured to surround a nerve 510 and position the two or more electrodes in electrical communication with the never. In the embodiment illustrated in FIG. 5, the electrodes are positioned along the bottom of the body 502 in contact with the nerve 510. In some embodiments, the two or more electrodes are in physical contact with the nerve, although some movement of the implantable device may be allowed so long as the electrodes remain in electrical communication with the nerve. The electrodes need not penetrate the epineurium of the nerve.

The clip includes a first leg 512 and a second leg 514, which are positioned on opposite sides of the nerve 510. The legs of the clip are optionally flexible so that the legs can be flexed outwardly to position the clip on the nerve. When the legs are released, the legs spring inwardly to maintain the electrodes in electrical communication with the nerve. The size and spacing of the legs can be set depending on the size of the nerve. In embodiment illustrated in FIG. 5, leg 514 has a width approximately the same length as the body 502. The leg 514 includes a first segment 516 that extends from the body along the side of the nerve 510 to below the nerve 510, and a second segment 518 that extends from the bottom of the first portion toward the underside of the nerve 510. A flexible member 520 (such as a hinge, which may be a spring hinge) joins the first segment 516 and the second segment 518, which can allow the second segment 518 to flex toward the first segment 516 when the implantable device is being positioned on the nerve. The end of second segment 518 can be released and the second segment 518 springs into position below the nerve 510. Optionally, a second flexible member 522 (which may be, for example, a hinge, which may be a spring hinge) attaches the leg 508 to the body 502. The second flexible member 522 allows the leg 514 to flex outwardly when positioning the implantable device on the nerve 510.

FIG. 6 shows another example of an implantable device, which includes a body 602 and a clip configured to at least partially surround a nerve, comprising a plurality of flexible legs 604, 606, 608, and 610. The body 602 includes a housing, and contains an ultrasonic transducer configured to receive ultrasonic waves and convert energy from the ultrasonic waves into an electrical energy that powers the implantable device. The implantable device further includes a plurality of electrodes positioned on the bottom of the body housing. The electrodes are in electrical communication with the ultrasonic transducer, for example through an integrated circuit contained within the body 602 of the implantable device. When the clip is positioned on the nerve to at least partially surround the nerve, the electrodes are positioned to be in electrical communication with the nerve.

The legs 604, 606, 608, and 610 of the implantable device extend below the body 602 and are curved, which allows the legs to wrap around the nerve and any filamentous tissue (e.g., a blood vessel) that may be attached to the nerve. The upper portion of the legs extend away from the body 602, and the legs curve back toward the body 602 as they extend below the body. The clip illustrated in FIG. 6 includes a first pair of legs, 604 and 606, and a second pair of legs 608 and 610. The paired legs extend away from the body in opposite directions. The upper portion of legs 604 and 606 are connected by crossbar 612, and the upper portion of legs 608 and 610 are connected by crossbar 614. Crossbar 612 is connected to the body 602 through flexible member 616, and crossbar 614 is connected to the body 602 through a second flexible member (not shown). The flexible member may be, for example, a hinge (which may be a spring hinge). The crossbars are connected to opposite sides of the body 602, and the length of the crossbars are oriented in the same direction (i.e., parallel to the nerve).

The size and shape of the clip can depend on the type and size of tissue that engages the clip. The clip is designed to allow the legs of the clip to at least partially surround filamentous tissue, such as a nerve or blood vessel. In some embodiments, such as the clip of the device shown in FIG. 6, the inner surface of the legs form a cylindrical space through which the nerve and/or filamentous tissue passes. The diameter of the cylindrical space formed by the legs depends on the target nerve and/or filamentous tissue that the implantable device will engage. In some embodiments, the legs of the device form a cylindrical space with a diameter of about 50 µm to about 15 mm (for example, about 50 µm to about 100 µm, about 100 µm to about 250 µm, about 250 µm to about 500 µm, about 500 µm to about 1 mm, about 1 mm to about 1.5 mm, about 1.5 mm to about 2.5 mm, about 2.5 mm to about 5 mm, about 5 mm to about 10 mm, or about 10 mm to about 15 mm). For example, a clip designed to at least partially surround the splenic nerve of a human can include curved legs that form a cylindrical space with a diameter of about 500 µm to about 1.5 mm. The legs of device may also be sized to optimally engage the nerve, and in some embodiments may have a width (including any coating material on the legs) of about 100 µm to about 4 mm (such as about 100 µm to about 200 µm, about 200 µm to about 400 µm, about 400 µm to about 1 mm, about 1 mm to about 2 mm, about 2 mm to about 3 mm, or about 3 mm to about 4 mm). In some embodiments, a clip designed to at least partially surround the splenic nerve of a human can include legs with a width of about 200 µm to about 2 mm.

As some nerves may be attached to a filamentous tissue, such as a blood vessel, the clip can be designed to at least partially surround the nerve and the filamentous tissue. In some embodiments, a clip configured to at least partially surround a nerve attached to a filamentous tissue (such as a blood vessel) can include curved legs that form a cylindrical space with a diameter of about 1 mm to about 10 mm (such as about 1 mm to about 2 mm, about 2 mm to about 3 mm, about 3 mm to about 4 mm, about 4 mm to about 5 mm, about 5 mm to about 6 mm, about 6 mm to about 7 mm, about 7 mm to about 8 mm, about 8 mm to about 9 mm, or about 9 mm to about 10 mm). For example, a clip configured to engage a splenic nerve attached to a splenic artery can include curved legs that form a cylindrical space with a diameter of about 2 mm to about 8 mm. The legs of device may also be sized to optimally engage the nerve and the filamentous tissue (such as a blood vessel), and in some embodiments may have a width (including any coating material on the legs) of about 100 µm to about 4 mm (such as about 100 µm to about 200 µm, about 200 µm to about 400 µm, about 400 µm to about 1 mm, about 1 mm to about 2 mm, about 2 mm to about 3 mm, or about 3 mm to about 4 mm). In some embodiments, a clip designed to at least partially surround the splenic nerve and the splenic artery of a human can include legs with a width of about 500 µm to about 2 mm.

FIG. 7 shows a side view of another embodiment of an implantable device with a clip. Similar to the implantable device shown in FIG. 6, the implantable device includes a body 702 with a clip configured to at least partially surround a nerve. The clip includes legs 704 and 706, although it is contemplated that the device optionally includes additional legs and/or one or more crossbars. The bottom surface 708 of the housing 702 includes feedthroughs 710, 712, and 714. The feedthroughs electrically connect the integrated circuit in the body of the device to the electrodes. For example, feedthrough 710 is electrically connected to electrode 716 through connection 718, and feedthrough 714 is electrically connected to electrode 720 through connection 722. The connections 718 and 722 may be, for example, a solder, a weld, or a crimp connecting the feedthrough to the electrode. Electrode 716 is positioned on the internal surface of leg 704, and electrode 720 is positioned on the internal surface of leg 706. The electrodes are in electrical communication with the ultrasonic transducer, for example through an integrated circuit contained within the body 702 of the implantable device via the feedthroughs. When the clip is positioned on the nerve to at least partially surround the nerve, the electrodes are positioned to be in electrical communication with the nerve. Leg 704 and leg 706 are secured to the body 702 of the device through a sealing material 724. The sealing material can also seal the connections 718 and 722. In some embodiments, the sealing material is an epoxy or a polymer (such as silicone or a urethane polymer).

The legs of the implantable device can comprise a metal, metal alloy, ceramic, silicon, or a non-polymeric material. In some embodiments, one or more electrodes are positioned on an inner surface of the legs. The legs are flexible, and preferably sprung such that the legs can be positioned around the nerve and/or filamentous tissue. In some embodiments, the legs or a portion of the legs are coated with an elastomeric coating or a non-elastomeric coating, which is preferably bioinert, such as polydimethylsioloxane (PDMS), a silicone, a urethane polymer, a poly(p-xylylene)polymer (such as a poly(p-xylylene) polymer sold under the tradename PARYLENE®), or a polyimide. In some embodiments, the implantable device includes one or more electrodes on the inner surface of the legs. In some embodiments, one or more of the electrodes on the inner surface of the legs are not coated with the elastomeric coating or the non-elastomeric polymer coating, although may be coated with a conductive material (e.g., electroplated with a PEDOT polymer or a metal to improve electrical characteristics of the electrode). Accordingly, in some embodiments, only the outer surface of the legs is coated with the coating. Optionally, the coating further coats the housing of the body. Referring to FIG. 7 by way of example, the outer surface of legs 704 and 706 are coated with the coating 726. However, because electrodes 716 and 720 are on the inner surface of legs 704 and 706, the coating 726 does not coat the inner surface of the legs.

FIG. 8A and FIG. 8B illustrate two exemplary configurations with electrodes on the legs of the clips. As shown in FIG. 8A, the leg 802 is coated with a coating 804, such as an elastomeric polymer or a non-elastomeric polymer. A single electrode is exposed through the elastomeric or non-elastomeric polymer, which can be in electrical communication with a nerve. FIG. 8B illustrates a leg 806 with a plurality of electrodes 808 along the inner surface of the leg. In the embodiment illustrated in FIG. 8B, the leg 806 is not coated with an elastomeric polymer or a non-elastomeric polymer. However, the leg 806 could be optionally coated with the polymer on the outer surface of the leg 806.

In some embodiments, the legs comprise one or more hooks or loops, which may be positioned proximal to the terminus of the legs or may be positioned along the length of the leg. The hook or loop can be used to help manipulate, flex, or position the clip into position. In some embodiments, the hook or loop curves toward the body of the implantable device, and in some embodiments the hook or loop curves away from the body of the implantable device. FIG. 9A shows one embodiment of a leg with a hook at the terminus of the leg. The leg 902 connects to the body of the device at the starting end 904, and extends below and away from the body. The leg 902 curves inwardly at 906 before curving outwardly at 908 to form a hook 910 at the terminus 912 of the leg. In some embodiments, the clip includes a hook or a loop configured to manipulate a leg of the clip, for example as shown in FIG. 9B. The implantable device includes a body 914 attached to a leg 916 that extends below and away from the body 914. The leg 916 is connected to a hook 918 opposite the body 914, for example through a continuous member (for example, metal or non-elastomeric plastic). The hook 918 and the leg 916 may be, for example, co-extruded or co-printed to form the continuous member. When hook 918 is pushed downwardly, the leg 916 is pushed outwardly. Through this mechanism, the implantable device can be properly positioned on a nerve, for example through laparoscopic implantation.

The two or more electrodes of the implantable device are positioned by the clip to be in electrical communication with the nerve. In some embodiments, the two or more electrodes directly contact the nerve. In some embodiments, the two or more electrodes are positioned within about 2 mm (within about 1.8 mm, within about 1.6 mm, within about 1.4 mm, within about 1.2 mm, within about 1.0 mm, within about 0.8 mm, within about 0.6 mm, within about 0.4 mm, or within about 0.2 mm of the nerve. The electrodes may be disposed on the bottom of the body or on one or more clip legs. Legs that extend below the body secure the body to the nerve, and by positioning the electrodes on the bottom of the body, the electrodes are positioned in electrical communication with the nerve.

Interrogator

The interrogator can wirelessly communicate with one or more implantable devices using ultrasonic waves, which are used to power and/or operate the implantable device. For example, the interrogator can transmit ultrasonic waves that encode instructions for operating the device, such as a trigger signal that instructs the implantable device to emit an electrical pulse. The interrogator can further receive ultrasonic backscatter from the implantable device, which encodes information transmitted by the implantable device. The information may include, for example, information related to a detected electrophysiological pulse, an electrical pulse emitted by the implantable device, and/or a measured physiological condition. The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. In some embodiments, the ultrasound transmitting function is separated from the ultrasound receiving function on separate devices. That is, optionally, the interrogator comprises a first device that transmits ultrasonic waves to the implantable device, and a second device that receives ultrasonic backscatter from the implantable device. In some embodiments, the transducers in the array can have regular spacing, irregular spacing, or be sparsely placed. In some embodiments the array is flexible. In some embodiments the array is planar, and in some embodiments the array is non-planar.

An exemplary interrogator is shown in FIG. 10. The illustrated interrogator shows a transducer array with a plurality of ultrasonic transducers. In some embodiments, the transducer array includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more transducers. In some embodiments, the transducer array includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer transducers. The transducer array can be, for example a chip comprising 50 or more ultrasonic transducer pixels.

The interrogator shown in FIG. 10 illustrates a single transducer array; however the interrogator can include 1 or more, 2 or more, or 3 or more separate arrays. In some embodiments, the interrogator includes 10 or fewer transducer arrays (such as 9, 8, 7, 6, 5, 4, 3, 2, or 1 transducer arrays). The separate arrays, for example, can be placed at different points of a subject, and can communicate to the same or different implantable devices. In some embodiments, the arrays are located on opposite sides of an implantable device. The interrogator can include an application specific integrated circuit (ASIC), which includes a channel for each transducer in the transducer array. In some embodiments, the channel includes a switch (indicated in FIG. 10 by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit.

In some embodiments, the transducer connected to the channel is configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. In some embodiments, the data representing the wave shape and frequency for each channel can be stored in a 'wave table'. This allows the transmit waveform on each channel to be different. Then, delay control and level shifters can be used to 'stream' out this data to the actual transmit signals to the transducer array. In some embodiments, the transmit waveform for each channel can be produced directly by a high-speed serial output of a microcontroller or other digital system and sent to the transducer element through a level shifter or high-voltage amplifier. In some embodiments, the ASIC includes a charge pump (illustrated in FIG. 10) to convert a first voltage supplied to the ASIC to a higher second voltage, which is applied to the channel. The channels can be controlled by a controller, such as a digital controller, which operates the delay control.

In the ultrasound receiving circuit, the received ultrasonic waves are converted to current by the transducers (set in a receiving mode), which is transmitted to a data capture circuit. In some embodiments, an amplifier, an analog-to-digital converter (ADC), a variable-gain-amplifier, or a time-gain-controlled variable-gain-amplifier which compensates for tissue loss, and/or a band pass filter is included in the receiving circuit. The ASIC can draw power from a power supply, such as a battery (which is preferred for a wearable embodiment of the interrogator). In the embodiment illustrated in FIG. 10, a 1.8V supply is provided to the ASIC, which is increased by the charge pump to 32V, although any suitable voltage can be used. In some embodiments, the interrogator includes a processor and or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, the transducer array contains more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

In some embodiments, the interrogator is implantable. In some embodiments, the interrogator is external (i.e., not implanted). By way of example, the external interrogator can be a wearable, which may be fixed to the body by a strap or adhesive. In another example, the external interrogator can be a wand, which may be held by a user (such as a healthcare professional). In some embodiments, the interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator.

The specific design of the transducer array depends on the desired penetration depth, aperture size, and size of the individual transducers within the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and λ is the wavelength of ultrasound in the propagation medium (i.e., the tissue). As understood in the art, the Rayleigh distance is the distance at which the beam radiated by the array is fully formed. That is, the pressure filed converges to a natural focus at the Rayleigh distance in order to maximize the received power. Therefore, in some embodiments, the implantable device is approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., *Beamforming Approaches for Untethered, Ultrasonic Neural Dust Motes for Cortical Recording: a Simulation Study*, IEEE EMBC (August 2014). In some embodiments, beam steering is performed by adjusting the power or phase of the ultrasonic waves emitted by the transducers in an array.

In some embodiments, the interrogator includes one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Optionally, the interrogator is controlled using a separate computer system, such as a mobile device (e.g., a smartphone or a table). The computer system can wirelessly communicate to the interrogator, for example through a network connection, a radiofrequency (RF) connection, or Bluetooth. The computer system may, for example, turn on or off the interrogator or analyze information encoded in ultrasonic waves received by the interrogator.

Communication Between an Implantable Device and an Interrogator

The implantable device and the interrogator wirelessly communicate with each other using ultrasonic waves. The implantable device receives ultrasonic waves from the interrogator through one or more ultrasonic transducers on the implantable device, and the ultrasonic waves can encode instructions for operating the implantable device. Vibrations of the ultrasonic transducer(s) on the implantable device generate a voltage across the electric terminals of the transducer, and current flows through the device, including the integrated circuit. The current can be used to charge an energy storage circuit, which can store energy to be used to emit an electrical pulse, for example after receiving a trigger signal. The trigger signal can be transmitted from the interrogator to the implantable device, signaling that an electrical pulse should be emitted. In some embodiments, the trigger signal includes information regarding the electrical pulse to be emitted, such as frequency, amplitude, pulse length, or pulse shape (e.g., alternating current, direct current, or pulse pattern). A digital circuit can decipher the trigger signal and operate the electrodes and electrical storage circuit to emit the pulse.

In some embodiments, ultrasonic backscatter is emitted from the implantable device, which can encode information relating to the implantable device, the electrical pulse emitted by the implantable device, an electrophysiological pulse detected by the implantable device, or a detected physiological condition. For example, the ultrasonic backscatter can encode a verification signal, which verifies that electrical pulse was emitted. In some embodiments, an implantable device is configured to detect an electrophysiological signal, and information regarding the detected electrophysiological signal can be transmitted to the interrogator by the ultrasonic backscatter. To encode signals in the ultrasonic backscatter, current flowing through the ultrasonic transducer(s) of the implantable device is modulated as a function of the encoded information, such as a detected electrophysiological signal or measured physiological condition. In some embodiments, modulation of the current can be an analog signal, which may be, for example, directly modulated by the detected electrophysiological signal. In some embodiments, modulation of the current encodes a digitized signal, which may be controlled by a digital circuit in the integrated circuit. The backscatter is received by an external ultrasonic transceiver (which may be the same or different from the external ultrasonic transceiver that transmitted the initial ultrasonic waves). The information from the electrophysiological signal can thus be encoded by changes in amplitude, frequency, or phase of the backscattered ultrasound waves.

FIG. 11 shows an interrogator in communication with an implantable device. The external ultrasonic transceiver emits ultrasonic waves ("carrier waves"), which can pass through tissue. The carrier waves cause mechanical vibrations on the ultrasonic transducer (e.g., a bulk piezoelectric transducer, a PUMT, or a CMUT). A voltage across the ultrasonic transducer is generated, which imparts a current flowing through an integrated circuit on the implantable device. The current flowing through to the ultrasonic transducer causes the transducer on the implantable device to emit backscatter ultrasonic waves. In some embodiments, the integrated circuit modulates the current flowing through the ultrasonic transducer to encode information, and the resulting ultrasonic backscatter waves encode the information. The backscatter waves can be detected by the interrogator, and can be analyzed to interpret information encoded in the ultrasonic backscatter.

Communication between the interrogator and the implantable device can use a pulse-echo method of transmitting and receiving ultrasonic waves. In the pulse-echo method, the interrogator transmits a series of interrogation pulses at a predetermined frequency, and then receives backscatter echoes from the implanted device. In some embodiments, the pulses are square, rectangular, triangular, sawtooth, or sinusoidal. In some embodiments, the pulses output can be two-level (GND and POS), three-level (GND, NEG, POS), 5-level, or any other multiple-level (for example, if using 24-bit DAC). In some embodiments, the pulses are continuously transmitted by the interrogator during operation. In some embodiments, when the pulses are continuously transmitted by the interrogator a portion of the transducers on the interrogator are configured to receive ultrasonic waves and a portion of the transducers on the interrogator are configured to transmit ultrasonic waves. Transducers configured to receive ultrasonic waves and transducers configured to transmit ultrasonic waves can be on the same transducer array or on different transducer arrays of the interrogator. In some embodiments, a transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period.

In some embodiments, the backscattered ultrasound is digitized by the implantable device. For example, the implantable device can include an oscilloscope or analog-to-digital converter (ADC) and/or a memory, which can digitally encode information in current (or impedance) fluctuations. The digitized current fluctuations, which can encode information, are received by the ultrasonic transducer, which then transmits digitized acoustic waves. The digitized data can compress the analog data, for example by using singular value decomposition (SVD) and least squares-based compression. In some embodiments, the compression is performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

In some embodiments, the digitized data can include a unique identifier. The unique identifier can be useful, for example, in a system comprising a plurality of implantable devices and/or an implantable device comprising a plurality of electrode pairs. For example, the unique identifier can identify the implantable device of origin when from a plurality of implantable devices, for example when transmitting information from the implantable device (such as a verification signal). In some embodiments, an implantable device comprises a plurality of electrode pairs, which may simultaneously or alternatively emit an electrical pulse by a single implantable device. Different pairs of electrodes, for example, can be configured to emit an electrical pulse in different tissues (e.g., different nerves or different muscles) or in different regions of the same tissue. The digitized circuit can encode a unique identifier to identify and/or verify which electrode pairs emitted the electrical pulse.

In some embodiments, the digitized signal compresses the size of the analog signal. The decreased size of the digitized signal can allow for more efficient reporting of information encoded in the ultrasonic backscatter. By compressing the size of the transmitted information through digitization, potentially overlapping signals can be accurately transmitted.

In some embodiments, an interrogator communicates with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. The interrogator can receive a combined backscatter from the plurality of the implantable devices, which can be deconvoluted, thereby extracting information from each implantable device. In some embodiments, interrogator focuses the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. In some embodiments, the interrogator transmits ultrasonic waves to a plurality of implantable devices, and then receives ultrasonic waves from the plurality of implantable devices.

Methods of Implanting the Implantable Device

The implantable device having a body and a clip attached to the body can be implanted in a subject to maneuver the legs of the clip to at least partially surround a nerve and/or filamentous tissue attached to the nerve, such as a blood vessel or tendon. The body includes one or more ultrasonic transducers configured to receive ultrasonic waves and convert energy from the ultrasonic waves into an electrical energy that powers the device. The device further includes one or more electrodes in electrical communication with the ultrasonic transducer, for example through an integrated circuit as described herein. The electrodes may be positioned on the legs of the implantable device, or on the body (such as underneath the body) of the implantable device. In some embodiments, the device is laparoscopically implanted.

In one example, implanting the device in a subject can include outwardly flexing one or more of the legs of the clip, and positioning the electrodes to be in electrical communication with the nerve. In some embodiments, the electrodes are positioned to directly contact the nerve. In some embodiments, the two or more electrodes are positioned within about 2 mm (within about 1.8 mm, within about 1.6 mm, within about 1.4 mm, within about 1.2 mm, within about 1.0 mm, within about 0.8 mm, within about 0.6 mm, within about 0.4 mm, or within about 0.2 mm of the nerve. The one or more flexed legs are released to allow the legs of the clam to at least partially surround the nerve and/or filamentous tissue attached to the nerve. With the legs partially surrounding the nerve, the electrodes are maintained in electrical communication with the nerve once the legs are released.

The implantable device may include one or more hooks or loops configured to maneuver one or more legs of the clip. For example, as shown in FIG. 9B, hook 918 can be pushed downward to force leg 916 to flex outwardly. With leg 916 flexed outwardly, the implantable device can be positioned to put the electrodes (which may be on leg 916 or on body 914) in electrical communication with the nerve. Hook 918 can be released, which releases leg 916 and allows leg 916 to close inwardly, thereby at least partially surrounding the nerve. The hooks or loops may be pushed upwardly, pushed downwardly, pushed laterally, or pulled to maneuver the legs of the clip.

The implantable device can be implanted so that the electrodes are in contact with, or the legs of the clip at least partially surround, an autonomic nerve. In some embodiments, the nerve is a sympathetic nerve, In some embodiments, the never is a vagus nerve, a mesenteric nerve, a splenic nerve, a sciatic nerve, a tibial nerve, a pudendal nerve, a celiac ganglion, a sacral nerve, or any branch thereof.

Methods of Using the Implantable Device

The implantable device is operated using an interrogator, which can transmit ultrasonic waves that power and operate the implantable device. The implantable device can be used in at least one of three basic modes of operation. First, the implantable device can be operated to emit an electrical pulse to a tissue. The electrical pulse may be applied to a nerve to stimulate neural activity or to block neural activity. Optionally, the electrically pulse may be emitted in response to the implantable device receiving a trigger signal encoded in ultrasonic waves transmitted by an interrogator. Further, the implantable device optionally encodes information related to the emitted electrical pulse (such as an affirmation that the pulse was emitted, a voltage of the pulse, or a pulse frequency) in ultrasonic backscatter waves, which can be received by an interrogator and analyzed to decode the information. Second, the implantable device can be operated to detect neural activity and transmit information related to the detected neural activity. Electrodes on the implantable device in electrical communication with a nerve can detect an electrophysiological pulse from the nerve, and information related to the electrophysiological pulse (e.g., frequency, voltage, shape, etc.) is encoded in the ultrasonic backscatter waves emitted by the one or more ultrasonic transducers on the implantable device. The ultrasonic backscatter waves encoding the information can be received by an interrogator and analyzed to decode the information. Third, the implantable device may include a sensor that can measure a physiological condition (e.g., pH, temperature, strain, tissue impedance, or concentration of an analyte, such as oxygen), and information related to the measured physiological condition may be encoded in ultrasonic backscatter waves emitted by the implantable device. The ultrasonic backscatter waves encoding information related to the measured physiological condition can be received by an interrogator and analyzed to decode the information related to the physiological condition.

In some embodiments, the three modes of operation support each other in the device to safely treat a medical condition. For example, the interrogator may transmit a trigger signal in ultrasonic waves based on information received by the implantable device relating to a measured physiological condition or a detected electrophysiological pulse. For example, an irregular electrophysiological pulse or electrophysiological pulse pattern may be treated by emitting one or more electrical pulses from the implantable device. The implantable device may detect one or more electrophysiological pulses from a nerve, and emit an ultrasonic backscatter encoding information related to the electrophysiological pulse. The ultrasonic backscatter can be received by an interrogator, which decodes the information and recognizes the electrophysiological pulse or electrophysiological pulse pattern as indicative of the need for an electrical pulse to be applied to the nerve. The interrogator can then transmit a trigger signal encoded in ultrasonic waves to the implantable device, thereby operating the implantable device to emit an electrical pulse. The measured physiological condition may also impact the decision of whether to operate the implantable device to emit an electrical pulse. For example, an elevated temperature measured by the implantable device may indicate that the electrical pulse should not be emitted. The interrogator may therefore transmit the trigger signal based on the detected electrophysiological pulse or electrophysiological pulse pattern, and/or the measured physiological condition.

The trigger signal transmitted by the interrogator can include instructions for emitting the electrical pulse, and may include instructions for the type of pulse (e.g., direct current pulse or alternating current pulse), a number pulses, a dwell time between pulses, a pulse frequency, a pulse amplitude, a pulse shape, or a pulse voltage. As discussed above, transmission of the trigger signal may be based on information related to a detected electrophysiological pulse, detected electrophysiological pulse pattern, or a measured physiological condition.

In some embodiments, the electrical pulse emitted by the implantable device is a direct current pulse or an alternating current pulse. In some embodiments, the electrical pulse comprises a plurality of pulses, which may be separated by a dwell time. In some embodiments, the electrical pulse is about 1 microsecond (µs) or longer (such as about 5 µs or longer, about 10 µs or longer, about 20 µs or longer, about 50 µs or longer, about 100 µs or longer, about 250 µs or longer, about 500 µs or longer, about 1 millisecond (ms) or longer, about 5 ms or longer, about 10 ms or longer, about 25 ms or longer, about 50 ms or longer, about 100 ms or longer, about 200 ms or longer, or about 500 ms or longer). In some embodiments, the electrical pulse is about 1000 ms or shorter (such as about 500 ms or shorter, about 200 ms or shorter, about 100 ms or shorter, or about 50 ms or shorter, about 25 ms or shorter, about 10 ms or shorter, about 5 ms or shorter, about 1 ms or shorter, about 500 µs or shorter, about 250 µs or shorter, about 100 µs or shorter, about 50 µs or shorter, about 20 µs or shorter, about 10 µs or shorter, or about 5 µs or shorter). In some embodiments, the dwell time is about 1 microsecond (µs) or longer (such as about 5 µs or longer, about 10 µs or longer, about 20 µs or longer, about 50 µs or longer, about 100 µs or longer, about 250 µs or longer, about 500 µs or longer, about 1 millisecond (ms) or longer, about 5 ms or longer, about 10 ms or longer, about 25 ms or longer, or about 50 ms or longer). In some embodiments, the dwell time is about 100 ms or shorter (such as about 50 ms or shorter, about 25 ms or shorter, about 10 ms or shorter, about 5 ms or shorter, about 1 ms or shorter, about 500 µs or shorter, about 250 µs or shorter, about 100 µs or shorter, about 50 µs or shorter, about 20 µs or shorter, about 10 µs or shorter, or about 5 µs or shorter).

In some embodiments, the electrical pulse is about 1 microamp (µA) or more (such as about 5 µA or more, about 10 µA or more, about 25 µA or more, about 50 µA or more, about 100 µA or more, about 250 µA or more, about 500 µA or more, about 1 milliamp (mA) or more, about 5 mA or more, about 10 mA or more, or about 25 mA or more). In some embodiments, the electrical pulse is about 50 mA or less (such as about 25 mA or less, about 10 mA or less, about 5 mA or less, about 1 mA or less, about 500 µA or less, about 250 µA or less, about 100 µA or less, about 50 µA or less, about 25 µA or less, about 10 µA or less, about 5 µA or less, or about 1 µA or less.

In some embodiments, the electrical pulse has a current frequency of about 0.1 Hz or more (such as about 0.5 Hz or more, about 1 Hz or more, about 5 Hz or more, about 10 Hz or more, about 25 Hz or more, about 50 Hz or more, about 100 Hz or more, about 200 Hz or more, about 300 Hz or more, about 400 Hz or more, about 500 Hz or more about 600 Hz or more, about 700 Hz or more, about 800 Hz or more, about 1 kHz or more, about 2 kHz or more, or about 5 kHz or more). In some embodiments, the electrical pulse has a current frequency of about 10 kHz or less (such as about 5 kHz or less, about 2 kHz or less, about 1 kHz or less, about 800 Hz or less, about 700 Hz or less, about 600 Hz or less, about 500 Hz or less, about 400 Hz or less, about 300 Hz or less, about 200 Hz or less, about 100 Hz or less, about 50 Hz or less, about 25 Hz or less, about 10 Hz or less, about 5 Hz or less, about 1 Hz or less, or about 0.5 Hz or less).

In some embodiments, the implantable device generates a voltage pulse in the tissue. In some embodiments, the voltage is about 50 mV or more (such as about 100 mV or more, about 250 mV or more, about 500 mV or more about 1 V or more, about 2.5 V or more, about 5 V or more, or about 10 V or more). In some embodiments, the voltage is about 20 V or less (such as about 15 V or less, about 10 V or less, about 5 V or less, about 2.5 V or less, about 1 V or less, about 500 mV or less, about 250 mV or less, or about 100 mV or less).

Features of the electrical pulse, such as frequency, amplitude, and length, can affect the impact of the electrical pulse on the neural tissue. For example, lower frequency pulses (such as those less than about 1 kHz) can stimulate neural activity, whereas higher frequency pulses (such as those greater than about 1 kHz) can block neural activity.

Methods of Treating Incontinence

In some embodiments, the implantable device described herein is used to treat incontinence in a patient, such as an overactive bladder, an underactive bladder, urinary incontinence, or fecal incontinence. The implantable device can be fully implanted in the subject such that the electrodes are in electrical communication with a tibial nerve or a branch thereof, a pudendal nerve or branch thereof, or a sacral nerve or a branch thereof, and the nerve can be electrically stimulated using the fully implanted medical device. In some embodiments, the implantable device electrically stimulates the nerve by emitting one or more electrical pulses that block neurological activity of the nerve. In some embodiments, the implantable device electrically stimulates the nerve by emitting one or more electrical pulses that activates neurological activity of the nerve. Electrical stimulation by emitting one or more electrical pulses (e.g., current pulses or voltage pulses) may be in response to a trigger signal encoded in ultrasonic waves received by the implantable device. As discussed above, transmission of the trigger signal may be based on a detected electrophysiological pulse or pulse pattern, or a measured physiological condition, which may be transmitted from the implantable device using ultrasonic backscatter.

The electrical pulses may be emitted by the implantable device at a constant frequency. The length of time that the electrical pulses are emitted may be predetermined, or may be based on a detected electrophysiological pulse or pulse pattern, or by a measured physiological condition, as described herein. In some embodiments, the frequency of the electrical pulses is between about 0.1 Hz and about 500 Hz, such as between about 0.2 Hz and about 250 Hz, between about 0.5 Hz and about 100 Hz, between about 1 Hz and about 50 Hz, or between about 5 Hz and about 30 Hz.

The interrogator can be externally worn by the subject, and can operate and power the implantable device, and the ultrasonic transducers on the interrogator preferably contact the skin of the subject. In some embodiments, the ultrasonic transducers of the interrogator are about 10 cm or less, about 5 cm or less, about 4 cm or less, about 3 cm or less, about 2 cm or less, or about 1 cm or less from the implantable device. Positioning of the interrogator depends on the positioning of the implantable device and which nerve is in electrical communication with the electrodes of the implantable device. For example, if the implantable device includes electrodes that are in electrical communication with a sacral nerve, the interrogator can be positioned on the hip, abdomen, lower back, buttocks, or upper leg of the patient. If the implantable device includes electrodes that are in electrical communication with a tibial nerve, the interrogator can be positioned on the lower leg (e.g., calf) or ankle of the subject. The interrogator can be positioned using an adhesive that fixes to the skin of the subject, a band, or can be a hand-held device positioned in the desired location.

By way of example, percutaneous tibial nerve stimulation (PTNS) is a known treatment for incontinence and related disorders, such as overactive bladder, urinary incontinence, and fecal incontinence. Known devices stimulate the tibial nerve by placing a needle electrode near the tibial nerve in the ankle by passing it through the skin. One lead of the device is connected to the exposed end of the electrode and the other lead is connected to a return electrode, which may be a conductive pad placed on the skin of the patient (such as on the foot). During treatment, current or voltage pulses are delivered at a constant frequency (for example, between 5 Hz and 30 Hz), and stimulation intensity is increased until there is movement in the patient's toe. Treatment continues for approximately 30 minutes, and is generally performed in a doctor's office once per week for 12 weeks, followed by longer interval maintenance treatments. Although this treatment is generally effective, there is substantial patient discomfort in regular needle insertions, and the treatment is inconvenient in that it requires frequent doctor visits. The system described herein provides a significantly more convenient treatment regimen, which can be performed in home and with increased frequency.

FIG. 13A shows an implantable device with a body and a clip fully implanted in a subject, wherein the clip attaches the implantable device to the tibial nerve. The body of the implantable device includes electrodes in electrical communication with the tibial nerve, and an ultrasonic transducer configured to receive ultrasonic waves that power and operate the device. The clip includes legs that surround the tibial nerve, and retain the electrodes in electrical contact with the nerve. The tibial nerve can be stimulated by converting energy from ultrasonic waves into an electrical energy to power the device, and electrically stimulating the tibial nerve in response to a trigger signal encoded in the ultrasonic waves. The ultrasonic waves received by the device can be transmitted by an interrogator, as shown in FIG. 13B. The interrogator is worn by the patient at the ankle. As illustrated in FIG. 13B, the ultrasonic transducers of the interrogator are positioned against the skin. Optionally, the interrogator is controlled by a computer system, such as a mobile device.

Sacral nerve stimulation is another method known to be used to treat certain urinary disorders such as an overactive bladder. Treatment can include continuous electrical stimulation of the sacral nerve to increase a time interval between urinary voids and to reduce a feeling of urgency to void the bladder. Known devices for sacral nerve stimulation generally include leads that are placed near the sacral nerve connected to an implanted pulse generator that contains a battery. The device can be surgically placed under the skin, usually in the lower abdomen near the hip. However, because these devices require a battery, the battery can wear out, requiring surgery to replace the device. Further, the leads of the device can break, again requiring surgery to remove the broken lead and replace device. Further, the surgical pocket is relatively large, and is subject to infection. Because of these concerns, many patients elect not to undergo sacral nerve stimulation treatment. However, the implantable device described herein is much smaller than known devices, thereby minimizing risk of infection. Additionally, the small size of the device described herein allows the implantable device to be secured directly on the sacral nerve, thereby avoiding the need for electrical leads that are subject to breakage. Further, because the device is powered by ultrasonic waves, the device is batteryless and there is no need to remove the device due to a failing battery.

FIG. 14 shows the system being used for sacral nerve stimulation (SNS). The implantable device includes a body having an ultrasonic transducer, electrodes, and a clip. The clip surrounds the sacral nerve to position the electrode in electrical communication with the sacral nerve. The ultrasonic transducer on the implantable device is configured to receive ultrasonic waves that power and operate the device. For example, the ultrasonic waves can optionally include a trigger signal that instructs the device to stimulate the nerve. The implantable device may be configured to continuously stimulate the nerve, and the ultrasonic waves may instruct the implantable device to begin to stop continuous stimulation. The implantable device may also emit an ultrasonic backscatter that encodes information related to the status of the device or about electrical pulses emitted by the device. An external interrogator can be worn by the subject, which can transmit the ultrasonic waves to the implantable device. The interrogator may include a battery that can be replaced or recharged. Optionally, the interrogator communicates with a computer system, such as a mobile device (e.g., a smartphone or tablet), which can turn on or off the system.

EXEMPLARY EMBODIMENTS

Embodiment 1

An implantable medical device, comprising:
a body comprising an ultrasonic transducer configured to receive ultrasonic waves and convert energy from the ultrasonic waves into an electrical energy that powers the device;
two or more electrodes in electrical communication with the ultrasonic transducer; and
a clip attached to the body that is configured to at least partially surround a nerve and position the two or more electrodes in electrical communication with the nerve.

Embodiment 2

The implantable medical device of embodiment 1, wherein the clip is configured to at least partially surround the nerve and a filamentous tissue attached to the nerve.

Embodiment 3

The implantable medical device of embodiment 2, wherein the filamentous tissue is a blood vessel.

Embodiment 4

The implantable medical device of any one of embodiments 1-3, wherein the clip comprises a plurality of flexible legs that extend below the body.

Embodiment 5

The implantable device of embodiment 4, wherein the implantable device comprises a hook or loop configured to maneuver at least one of the flexible legs in response to maneuvering the hook or loop.

Embodiment 6

The implantable device of embodiment 5, wherein the hook or loop is positioned at a terminus of one of the flexible legs.

Embodiment 7

The implantable device of embodiment 5, wherein the hook or loop is positioned proximal to the body.

Embodiment 8

The implantable medical device of any one of embodiments 4-7, wherein the flexible legs are curved.

Embodiment 9

The implantable medical device of embodiment 8, wherein the legs extend away from the body before curving toward the body as the legs extend below the body.

Embodiment 10

The implantable medical device of embodiment 9, wherein the plurality of flexible legs comprises at least one pair of legs, wherein the pair of legs comprises a first leg and a second leg that extend away from and below the body in opposite directions.

Embodiment 11

The implantable medical device of embodiment 10, wherein the first leg and the second leg are connected by a crossbar connected to the body.

Embodiment 12

The implantable medical device of embodiment 11, wherein the crossbar is connected to the body of the device through a flexible member.

Embodiment 13

The implantable medical device of embodiment 12, wherein the flexible member is a hinge.

Embodiment 14

The implantable medical device of any one of embodiments 10-13, wherein the device comprises two pairs of legs, wherein each pair of leg is positioned on opposite sides of the body.

Embodiment 15

The implantable medical device of any one of embodiments 4-14, wherein the legs are attached to the body through a bottom surface of the body.

Embodiment 16

The implantable medical device of any one of embodiments 4-14, wherein the legs are attached to the body through a sidewall of the body.

Embodiment 17

The implantable medical device of any one of embodiments 4-16, wherein the legs comprise a metal, metal alloy, ceramic, silicon, or a non-polymeric material.

Embodiment 18

The implantable medical device of any one of embodiments 4-17, wherein the legs comprise an elastomeric coating or a non-elastomeric polymer coating.

Embodiment 19

The implantable medical device of embodiment 18, wherein the coating is bioinert.

Embodiment 20

The implantable medical device of embodiment 18 or 19, wherein the coating is a silicone, a poly(p-xylylene) polymer, or a polyimide.

Embodiment 21

The implantable medical device of any one of embodiments 18-20, wherein at least one of the legs comprises an outer surface coated with the elastomeric coating or the non-elastomeric polymer coating and an inner surface comprising at least one electrode that is not coated with the elastomeric coating or the non-elastomeric polymer coating.

Embodiment 22

The implantable medical device of any one of embodiments 1-21, wherein the body comprises a bottom surface, and the two or more electrodes are terminate on the bottom of the body.

Embodiment 23

The implantable medical device of any one of embodiments 1-21, wherein the two or more electrodes are positioned on the clip.

Embodiment 24

The implantable medical device of embodiment 23, wherein the clip comprises a plurality of flexible legs that extend below the body, and the two or more electrodes are positioned on the flexible legs.

Embodiment 25

The implantable medical device of any one of embodiments 1-24, wherein the body comprises a housing.

Embodiment 26

The implantable medical device of embodiment 17, wherein the housing comprises or is coated with a bioinert material.

Embodiment 27

The implantable medical device of embodiment 26, wherein the housing comprises the bioinert material, and wherein the bioinert material of the housing comprises titanium or a ceramic.

Embodiment 28

The implantable medical device of any one of embodiments 1-27, wherein the body comprises an integrated circuit electrically connected to the ultrasonic transducer and the two or more electrodes.

Embodiment 29

The implantable medical device of embodiment 28, wherein the integrated circuit comprises an energy storage circuit comprising a capacitor.

Embodiment 30

The implantable medical device of any one of embodiments 1-29, wherein the body is about 5 mm or less in length in the longest dimension.

Embodiment 31

The implantable medical device of any one of embodiments 1-30, wherein the ultrasonic transducer is configured to emit an ultrasonic backscatter that encodes data.

Embodiment 32

The implantable medical device of embodiment 31, wherein the data comprises information related to a detected neural activity, a measured physiological condition, a device status, or an emitted electrical pulse.

Embodiment 33

The implantable medical device of any one of embodiments 1-32, wherein the implantable medical device is configured to emit an electrical pulse to the nerve.

Embodiment 34

The implantable medical device of any one of embodiments 1-33, wherein the ultrasonic transducer is configured to receive ultrasonic waves that encode instructions for operating the implantable device.

Embodiment 35

The implantable medical device of embodiment 34, wherein the instructions comprise a trigger signal that operates the implantable device to emit an electrical pulse to the nerve.

Embodiment 36

A method of implanting a medical device in a subject, the device comprising a body comprising an ultrasonic transducer configured to receive ultrasonic waves and convert energy from the ultrasonic waves into an electrical energy that powers the device, electrodes in electrical communication with the ultrasonic transducer, and a clip attached to the body, wherein the clip comprises a plurality of flexible legs, the method comprising:
outwardly flexing one or more legs of the clip;
positioning the electrodes to be in electrical communication with a nerve; and
releasing the one or more legs of the clip, where the one or more legs at least partially surrounds the nerve and maintains the electrodes in electrical communication with the nerve upon release.

Embodiment 37

The method of embodiment 36, wherein the plurality of legs at least partially surrounds the nerve and a filamentous tissue attached to the nerve.

Embodiment 38

The method of embodiment 37, wherein the filamentous tissue is a blood vessel.

Embodiment 39

The method of any one of embodiments 36-38, wherein the device is laparoscopically implanted in the subject.

Embodiment 40

The method of any one of embodiments 36-39, wherein the clip exerts an inward pressure on the nerve.

Embodiment 41

The method of any one of embodiments 36-40, wherein the clip allows for rotational movement around the nerve.

Embodiment 42

The method of any one of embodiments 36-41, wherein the nerve is an autonomic nerve.

Embodiment 43

The method of anyone of embodiments 36-42, wherein the nerve is a sympathetic nerve.

Embodiment 44

The method of any one of embodiments 36-43, wherein the nerve is a mesenteric nerve, a splenic nerve, a sciatic nerve, a tibial nerve, a celiac ganglion, or a sacral nerve.

Embodiment 45

The method of any one of embodiments 36-44, wherein the legs exert a pressure on the nerve or the filamentous tissue of about 1 MPa or less.

Embodiment 46

The method of any one of embodiments 36-45, wherein the plurality of legs extend below the body.

Embodiment 47

The method of any one of embodiments 36-46, wherein outwardly flexing one or more legs of the clip comprises maneuvering one or more hooks or loops connected to the one or more legs.

Embodiment 48

The method of any one of embodiments 36-47, wherein the legs are curved.

Embodiment 49

The method of any one of embodiments 36-48, wherein the legs extend away from the body before curving toward the body as the legs extend below the body.

Embodiment 50

The method of any one of embodiments 36-49, wherein the plurality of flexible legs comprises at least one pair of legs, wherein the pair of legs comprises a first leg and a second leg that extend away from and below the body in opposite directions.

Embodiment 51

The method of embodiment 50, wherein the pair of legs are connected by a crossbar connected to the body.

Embodiment 52

The method of embodiment 51, wherein the crossbar is connected to the body of the device through a flexible member.

Embodiment 53

The method of embodiment 52, wherein the flexible member is a hinge.

Embodiment 54

The method of any one of embodiments 36-53, wherein the device comprises two pairs of legs, wherein each pair of leg is positioned to opposite sides of the body.

Embodiment 55

The method of any one of embodiments 36-54, wherein the legs are attached to the body through a bottom surface of the body.

Embodiment 56

The method of any one of embodiments 36-54, wherein the legs are attached to the body through a sidewall of the body.

Embodiment 57

The method of any one of embodiments 36-56, wherein the legs comprise a metal, metal alloy, ceramic, silicon, or a non-polymeric material.

Embodiment 58

The method of any one of embodiments 36-57, wherein the legs comprise an elastomeric coating or a non-elastomeric polymer coating.

Embodiment 59

The method of embodiment 58, wherein the coating is bioinert.

Embodiment 60

The method of embodiment 58 or 59, wherein the coating is a silicone, a urethane polymer, a poly(p-xylylene) polymer, or a polyimide.

Embodiment 61

The method of any one of embodiments 58-60, wherein at least one of the legs comprises an outer surface coated with the elastomeric coating or the non-elastomeric polymer coating and an inner surface comprising at least one electrode that is not coated with the elastomeric coating or the non-elastomeric polymer coating.

Embodiment 62

The method of any one of embodiments 36-61, wherein the body comprises a bottom surface, and the two or more electrodes are terminate on the bottom of the body.

Embodiment 63

The method of any one of embodiments 36-61, wherein the two or more electrodes are positioned on the clip.

Embodiment 64

The method of embodiment 63, wherein the clip comprises a plurality of flexible legs that extend below the body, and the two or more electrodes are positioned on the flexible legs.

Embodiment 65

The method of any one of embodiments 36-64, wherein the body comprises a housing.

Embodiment 66

The method of embodiment 65, wherein the housing comprises a bioinert material.

Embodiment 67

The method of embodiment 66, wherein the housing comprises the bioinert material, and wherein the bioinert material of the housing comprises titanium or a ceramic.

Embodiment 68

The method of any one of embodiments 36-67, wherein the body comprises an integrated circuit electrically connected to the ultrasonic transducer and the two or more electrodes.

Embodiment 69

The method of embodiment 68, wherein the integrated circuit comprises an energy storage circuit comprising a capacitor.

Embodiment 70

The method of any one of embodiments 36-69, wherein the body is about 5 mm or less in length in the longest dimension.

Embodiment 71

An implantable medical device, comprising:
(a) two or more ultrasonic transducers configured to receive ultrasonic waves that power the device and emit an ultrasonic backscatter;
(b) an integrated circuit comprising an energy storage circuit comprising a capacitor, wherein the integrated circuit is electrically connected to the first ultrasonic transducer and the second ultrasonic transducer; and
(c) one or more of (i) a sensor configured to measure a physiological condition, (ii) two or more electrodes configured to be in electrical communication with a tissue and emit an electrical pulse to the tissue, or (iii) two or more electrodes configured to be in electrical communication with a tissue and detect an electrophysiological signal from the tissue;
wherein the sensor or the two or more electrodes are electrically connected to the integrated circuit.

Embodiment 72

The implantable medical device of embodiment 71, wherein the two or more ultrasonic transducers comprise a first ultrasonic transducer comprising a first polarization axis and a second ultrasonic transducer comprising a second polarization axis, wherein the second ultrasonic transducer is positioned so that the second polarization axis is orthogonal to the first polarization axis, and wherein the first ultrasonic transducer and the second ultrasonic transducer are configured to receive the ultrasonic waves that power the device and emit the ultrasonic backscatter.

Embodiment 73

The implantable medical device of embodiment 71 and 72, wherein the implantable device comprises the sensor configured to measure a physiological condition.

Embodiment 74

The implantable medical device of embodiment 73, wherein the sensor is a temperature sensor, a pH sensor, a pressure sensor, a strain sensor, a pulse sensor, a blood pressure sensor, an oxygen meter, a glucose meter, an impedance meter, or is configured to measure an analyte concentration.

Embodiment 75

The implantable medical device of embodiment 71 or 72, wherein the implantable device comprises the two or more electrodes configured to be in electrical communication with a tissue and emit an electrical pulse to the tissue.

Embodiment 76

The implantable medical device of embodiment 75, wherein the implantable device comprises the two or more electrodes configured to be in electrical communication with a tissue and detect an electrophysiological signal from the tissue.

Embodiment 77

The implantable medical device of embodiment 76, wherein the electrophysiological signal is a neural signal.

Embodiment 78

The implantable medical device of any one of embodiments 71-77, wherein the ultrasonic backscatter encodes information related to the measured physiological condition, the emitted electrical pulse, or the detected electrophysiological signal.

Embodiment 79

The implantable medical device of embodiment 78, wherein the two or more ultrasonic transducers are electrically connected to the integrated circuit in parallel.

Embodiment 80

The implantable medical device of any one of embodiments 71-79, wherein the two or more ultrasonic transducers and the integrated circuit are contained within a body, the device further comprising a clip configured to at least partially surround a filamentous tissue.

Embodiment 81

The implantable medical device of embodiment 80, wherein the filamentous tissue comprises a nerve.

Embodiment 82

The implantable medical device of embodiment 80, wherein the filamentous tissue comprises a nerve attached to a blood vessel.

Embodiment 83

The implantable medical device of embodiment 80, wherein the filamentous tissue comprises a nerve attached to a blood vessel.

Embodiment 84

The implantable medical device of embodiment any one of embodiments 80-83, wherein the clip comprises a plurality of flexible legs that extend below the body.

Embodiment 85

The implantable medical device of any one of embodiments 1-35 and 71-84, wherein the implantable medical device does not comprise a battery.

Embodiment 86

The implantable medical device of any one of embodiments 1-35 and 71-85, wherein the implantable medical device does not comprise a radiofrequency communication system.

Embodiment 87

The implantable medical device of any one of embodiments 1-35 and 71-86, wherein the implanted medical device does not comprise an electrical lead that extends from the body of the device without terminating on a leg of a clip.

Embodiment 88

A system, comprising the implantable medical device of any one of embodiments 1-35 and 71-87, and an interrogator comprising one or more ultrasonic transducers configured to transmit ultrasonic waves to the implantable medical device, wherein the ultrasonic waves power the implantable medical device.

Embodiment 89

The system of embodiment 88, wherein the interrogator is configured to be worn externally.

Embodiment 90

The system of embodiment 88 or 89, wherein the interrogator is configured to receive ultrasonic backscatter emitted by the implantable device, wherein the ultrasonic backscatter encodes data.

Embodiment 91

The system of embodiment 90, wherein the interrogator is configured to analyze the data or transmit the data to a computer system.

Embodiment 92

The system of any one of embodiments 88-91, wherein the ultrasonic waves transmitted by the interrogator encode instructions for operating the implantable device.

Embodiment 93

A method of treating incontinence in a subject, comprising:
converting energy from ultrasonic waves into electrical energy that powers a fully implanted medical device in the subject, the device comprising two or more electrodes in electrical communication with a tibial nerve or a branch thereof, a pudendal nerve or a branch thereof, or a sacral nerve or a branch thereof of the subject; and
electrically stimulating the tibial nerve or the branch thereof, the pudendal nerve or the branch thereof, or the sacral nerve or the branch thereof, of the subject using the fully implanted medical device.

Embodiment 94

The method of embodiment 93, wherein the tibial nerve or the branch thereof, the pudendal nerve or the branch thereof, or the sacral nerve or the branch thereof is stimulated by the fully implanted medical device in response to a trigger signal encoded in the ultrasonic waves.

Embodiment 95

The method of embodiment 93 or 94, wherein electrically stimulating the tibial nerve or the branch thereof, the pudendal nerve or the branch thereof, or the sacral nerve or the branch thereof comprises emitting a plurality of current pulses to the tibial nerve or the branch thereof, the pudendal nerve or the branch thereof, or the sacral nerve or the branch thereof.

Embodiment 96

The method of embodiment 93 or 94, wherein electrically stimulating the tibial nerve or the branch thereof, the pudendal nerve or the branch thereof, or the sacral nerve or the branch thereof, comprises emitting a plurality of voltage pulses to the tibial nerve or the branch thereof, the pudendal nerve or the branch thereof, or the sacral nerve or the branch thereof.

Embodiment 97

The method of embodiment 95 or 96, wherein the plurality or current pulses or the plurality of voltage pulses are emitted at a constant frequency.

Embodiment 98

The method of embodiment 97, wherein the frequency of the plurality of current pulses or the plurality of voltage pulses is between about 1 Hz and about 50 Hz.

Embodiment 99

The method of any one of embodiments 93-98, comprising transmitting the ultrasonic waves to the implanted medical device using a interrogator comprising one or more ultrasonic transducers.

Embodiment 100

The method of embodiment 99, wherein the ultrasonic waves encode instructions for operating the implantable device.

Embodiment 101

The method of embodiment 99 or 100, comprising emitting an ultrasonic backscatter that encodes data.

Embodiment 102

The method of embodiment 101, wherein the data comprises a stimulation status that indicates whether the implantable device emitted an electrical pulse or what parameters were used to emit the electrical pulse.

Embodiment 103

The method of embodiment 101 or 102, comprising receiving the ultrasonic backscatter.

Embodiment 104

The method of embodiment 103, comprising analyzing the data encoded by the ultrasonic backscatter.

Embodiment 105

The method of any one of embodiments 93-104, wherein the interrogator is an externally worn device.

Embodiment 106

The method of any one of embodiments 93-105, wherein the interrogator contacts the skin of the subject.

Embodiment 107

The method of any one of embodiment 93-106, wherein the interrogator is operated using a handheld device.

Embodiment 108

The method of embodiment 107, wherein the handheld device is wirelessly connected to the interrogator.

Embodiment 109

The method of any one of embodiments 93-108, comprising implanting the medical device in the subject to contact the two or more electrodes to the tibial nerve or the branch thereof, the pudendal nerve or the branch thereof, or the sacral nerve or the branch thereof.

Embodiment 110

The method of any one of embodiments 93-109, wherein the two or more electrodes are in electrical communication with the tibial nerve or the branch thereof.

Embodiment 111

The method of embodiment 110, wherein the interrogator is attached to the ankle of the subject.

Embodiment 112

The method of any one of embodiments 93-109, wherein the two or more electrodes are in electrical communication with the sacral nerve or the branch thereof.

Embodiment 113

The method of embodiment 112, wherein the interrogator is attached the hip, abdomen, lower back, buttocks, or upper leg of the patient.

Embodiment 114

The method of any one of embodiments 93-113, wherein the incontinence is an overactive bladder, an underactive bladder, urinary incontinence, or fecal incontinence.

Embodiment 115

The method of any one of embodiments 93-114, wherein the subject is a human.

Embodiment 116

The method of any one of embodiments 93-115, wherein the implantable device is the implantable medical device according to any one of embodiments 1-35 and 71-87.

What is claimed is:

1. An implantable medical device, comprising:
   (a) two or more ultrasonic transducers configured to receive ultrasonic waves that power the device and emit an ultrasonic backscatter;
   (b) an integrated circuit comprising an energy storage circuit comprising a capacitor, wherein the integrated circuit is electrically connected to the first ultrasonic transducer and the second ultrasonic transducer; and
   (c) one or more of (i) a sensor configured to measure a physiological condition, (ii) two or more electrodes configured to be in electrical communication with a tissue and emit an electrical pulse to the tissue, or (iii) two or more electrodes configured to be in electrical communication with a tissue and detect an electrophysiological signal from the tissue;
   wherein the sensor or the two or more electrodes are electrically connected to the integrated circuit.

2. The implantable medical device of claim 1, wherein the two or more ultrasonic transducers comprise a first ultrasonic transducer comprising a first polarization axis and a second ultrasonic transducer comprising a second polarization axis, wherein the second ultrasonic transducer is positioned so that the second polarization axis is orthogonal to the first polarization axis, and wherein the first ultrasonic transducer and the second ultrasonic transducer are configured to receive the ultrasonic waves that power the device and emit the ultrasonic backscatter.

3. A system, comprising the implantable medical device of claim 1, and an interrogator comprising one or more ultrasonic transducers configured to transmit ultrasonic waves to the implantable medical device, wherein the ultrasonic waves power the implantable medical device.

4. The system of claim 3, wherein the interrogator is configured to be worn externally.

5. The system of claim 3, wherein the interrogator is configured to receive ultrasonic backscatter emitted by the implantable device, wherein the ultrasonic backscatter encodes data.

6. The system of claim 5, wherein the interrogator is configured to analyze the data or transmit the data to a computer system.

7. The system of claim 3, wherein the ultrasonic waves transmitted by the interrogator encode instructions for operating the implantable device.

8. The implantable medical device of claim 1, wherein the implantable device comprises the sensor configured to measure a physiological condition.

9. The implantable medical device of claim 8, wherein the sensor is a temperature sensor, a pH sensor, a pressure sensor, a strain sensor, a pulse sensor, a blood pressure sensor, an oxygen meter, a glucose meter, an impedance meter, or is configured to measure an analyte concentration.

10. The implantable medical device of claim 1, wherein the implantable device comprises the two or more electrodes configured to be in electrical communication with a tissue and emit an electrical pulse to the tissue.

11. The implantable medical device of claim 10, wherein the implantable device comprises the two or more electrodes configured to be in electrical communication with a tissue and detect an electrophysiological signal from the tissue.

12. The implantable medical device of claim 11, wherein the electrophysiological signal is a neural signal.

13. The implantable medical device of claim 1, wherein the ultrasonic backscatter encodes information related to the measured physiological condition, the emitted electrical pulse, or the detected electrophysiological signal.

14. The implantable medical device of claim 1, wherein the two or more ultrasonic transducers are electrically connected to the integrated circuit in parallel.

15. The implantable medical device of claim 1, wherein the implantable medical device does not comprise a battery.

16. The implantable medical device of claim 1, wherein the implantable medical device does not comprise a radiofrequency communication system.

17. The implantable medical device of claim 1, wherein the implanted medical device does not comprise an electrical lead that extends from the body of the device without terminating on a leg of a clip.

\* \* \* \* \*